US012708757B2

(12) United States Patent
Theran et al.

(10) Patent No.: US 12,708,757 B2
(45) Date of Patent: Aug. 18, 2026

(54) AXIAL FLOW PUMPS FOR SUPPORTING CARDIAC FUNCTION

(71) Applicant: Corisma Cardiovascular, Hamden, CT (US)

(72) Inventors: Michael Edward Theran, Bethany, CT (US); Jim Kelley, Hamden, CT (US); Mark Kelley, Hamden, CT (US)

(73) Assignee: Corisma Cardiovascular, Hamden, CT (US)

( * ) Notice: Subject to any disclaimer, the term of this patent is extended or adjusted under 35 U.S.C. 154(b) by 250 days.

(21) Appl. No.: 18/574,215

(22) PCT Filed: Jun. 27, 2022

(86) PCT No.: PCT/US2022/035172
§ 371 (c)(1),
(2) Date: Dec. 26, 2023

(87) PCT Pub. No.: WO2023/278351
PCT Pub. Date: Jan. 5, 2023

(65) Prior Publication Data

US 2024/0285927 A1 Aug. 29, 2024

Related U.S. Application Data

(60) Provisional application No. 63/318,559, filed on Mar. 10, 2022, provisional application No. 63/217,388, filed on Jul. 1, 2021.

(51) Int. Cl.
*A61M 60/17* (2021.01)
*A61M 60/226* (2021.01)
(Continued)

(52) U.S. Cl.
CPC .......... *A61M 60/17* (2021.01); *A61M 60/226* (2021.01); *A61M 60/416* (2021.01);
(Continued)

(58) Field of Classification Search
None
See application file for complete search history.

(56) References Cited

U.S. PATENT DOCUMENTS 5,527,159 A 6/1996 Bozeman, Jr. et al.
6,135,729 A 10/2000 Aber
(Continued)

OTHER PUBLICATIONS

International Preliminary Report on Patentability; International Application No. PCT/US2022/035172; Dec. 14, 2023.
(Continued)

*Primary Examiner* — Mallika D Fairchild
(74) *Attorney, Agent, or Firm* — Farber LLC

(57) ABSTRACT

The present disclosure provides a pump for supporting heart function, that includes a housing with a rotor disposed within the housing and spaced from an internal surface of the housing to define a clearance therebetween. An impeller is coupled to the rotor for propelling blood from a first inlet to an outlet of the housing along a primary blood flow path. The housing includes a second inlet fluidly coupled to the clearance between the rotor and the housing to define a secondary flow path through the clearance. The blood flowing through the secondary flow path continuously flushes the space between the rotor and the housing to minimize the formation and/or growth of blood clots and/or to remove heat generated by the pump. The secondary flow path may also provide a fluid bearing for the rotor and/or the impeller to reduce or eliminate contact surfaces and/or mechanical bearings between the rotating components of the pump and its housing, thereby reducing wear on these components and increasing the longevity of the pump.

21 Claims, 18 Drawing Sheets

(51) Int. Cl.

| | |
|---|---|
| ***A61M 60/416*** | (2021.01) |
| ***A61M 60/806*** | (2021.01) |
| ***A61M 60/81*** | (2021.01) |
| ***A61M 60/824*** | (2021.01) |
| ***A61M 60/861*** | (2021.01) |
| ***A61M 60/873*** | (2021.01) |
| ***A61M 60/90*** | (2021.01) |

(52) U.S. Cl.

CPC .......... *A61M 60/806* (2021.01); *A61M 60/81* (2021.01); *A61M 60/824* (2021.01); *A61M 60/861* (2021.01); *A61M 60/873* (2021.01); *A61M 60/90* (2021.01); *A61M 2205/04* (2013.01); *A61M 2205/103* (2013.01); *A61M 2206/10* (2013.01); *A61M 2210/125* (2013.01)

(56) References Cited

U.S. PATENT DOCUMENTS

| | | | | |
|---|---|---|---|---|
| 8,731,664 | B2 | 5/2014 | Foster et al. | |
| 10,918,774 | B2 | 2/2021 | Vadovations | |
| 2019/0125948 | A1* | 5/2019 | Stanfield ............... | A61M 60/13 |

OTHER PUBLICATIONS

International Search Report and Written Opinion; International Application No. PCT/US2022/035172; Sep. 15, 2022.

* cited by examiner 237
240
200
235
231
233
202

241
239
243
214
257
255
281
202
237

AXIAL FLOW PUMPS FOR SUPPORTING CARDIAC FUNCTION

CROSS-REFERENCE TO RELATED APPLICATIONS

This application is the National Stage of International Application No. PCT/US2022/035172, filed 27 Jun. 2022, which claims the benefit of U.S. Provisional Application Ser. No. 63/217,388, filed Jul. 2, 2021 and 63/318,559, filed Mar. 10, 2022, the entire disclosures of which are incorporated herein by reference in their entirety for all purposes.

FIELD

The present description generally relates to devices and methods for supporting cardiac function and more specifically to axial flow pumps designed for implantation into a heart chamber to assist or replace heart function.

BACKGROUND

In recent decades, the confluence of advances in medical and surgical capabilities, biomedical engineering, and electronic and computer miniaturization has produced a revolution in the field of active implantable medical devices, with resultant increases in human longevity and quality of life. Examples of implantable medical devices include artificial hearts, implantable heart monitors and defibrillators, pacemakers, artificial heart valves, neurostimulators, ventricular assist devices, extracorporeal membrane oxygenation devices (ECMO) and the like.

A ventricular assist device (VAD) is a medical device that partially or completely replaces the function of a damaged or failing heart. VADs typically assist the heart and do not completely take over cardiac function or require removal of the patient's heart. A particular VAD may be used to assist the patient's right ventricle (RVAD), left ventricle (LVAD) or both ventricles (BiVAD), depending on the needs of the patient.

VADs have an outer casing, which may be a collapsible stent design, and typically include an axial or radial flow pump within the casing to support cardiac function. The casing is typically implanted into one of the lower chambers of the heart, such as the left ventricle, where it receives blood. The pump includes a rotor with impeller blades that rotate and add work to the blood, propelling it from the device to the aorta for distribution to the rest of the body. Recently, systems have been designed to wirelessly power and control the axial pump, thereby obviating the need to implant a power source within the patient. In addition, VADs can be implanted using minimally invasive procedures without the need for open heart surgery.

Although VADs may sometimes be intended for short term use, for example, to provide post-operative assistance to a surgically repaired heart or as a bridge while awaiting a transplant, VADs are increasingly being used as a long-term solution. For example, VADs are now being implanted in patients suffering from congestive heart failure and for destination therapy (DT) for patients with heart failure who are no longer responding to optimal medical management and are not candidates for heart transplant surgery. The broadened use criteria of VADs coupled with a growing imbalance of transplant candidates and available hearts have resulted in an increased frequency of LVAD implantation and longer durations of support. As LVAD utilization grows, expectations of an improved and stable quality of life have become increasingly important as patients desire to return to a normal lifestyle and experience minimal disruptions from their LVADs. A large part of this expectation is based on the assumed reliability of the pump and its components.

While blood pumps have been effective for many patients, further improvements that prolong the effectiveness and lifetime of such blood pumps are desired. Implantable blood pumps should be compact so as to facilitate mounting the pump within the patient's body. They should also provide high reliability in prolonged use within the patient, most typically years, or even decades of service. An implantable blood pump should also be efficient so as to minimize the power required to operate the pump. This is particularly significant where, as in most applications, the pump is powered by a portable battery or other portable power source carried on or in the patient's body. Moreover, the pump should be designed to minimize damage to the patient's blood, exhibiting low hemolysis and good resistance to thrombosis.

One of the most common causes of pump malfunction in VADs is pump thrombosis, or the blockage in the flow of blood anywhere along a vessel upstream or downstream of the pump, or within the pump itself. Pump thrombosis can be caused by a variety of factors, including heat generated by the pump rotor, kinks in the outflow grafts, turbulent blood flow through the impeller, blood coagulation or clotting associated with blood-contacting surfaces of the device, such as the inflow cannula, the outflow graft, or components of the pump itself. For example, bearings that support the pump within the stent housing may create areas of thrombus that can be dislodged, possibly resulting in embolic stroke, increased hemolysis, circulatory failure or device dysfunction.

Another drawback with existing pumps for long-term use of VADs relates to the mechanical reliability of the pump itself. Conventional pumps typically suspend the rotor within the housing with mechanical bearings or bushings. Contact-type bearings may heat up during use and are subject to mechanical wear caused by the contact of the rotating bearing surface and the static bearing surface during operating of the pump. In addition, the bearings can cause blood damage and thrombosis.

Some of these issues have been resolved by suspending at least part of the rotor assembly with non-contact type bearings, such as a magnetic bearing in which the bearing surfaces "levitate" due to repelling magnetic forces. This creates clearance spaces between the rotor and housing that reduce wear on the pump components. However, blood flowing into these clearance spaces can become clotted or clogged, resulting in thrombosis. In addition, magnetic bearings require relatively large magnetic coils and associated electronics that create additional components for the pump and take up considerable space, which increases the overall footprint of the pump. Magnetic bearings also consume significant energy, creating larger power requirements for the overall device.

What is needed, therefore, are improved devices and methods for supporting heart function, such as intracardiac pumps that may, for example, be designed for a longer duration of support. In particular, it would be desirable to provide more compact implantable axial flow pumps that generate minimal wear from moving parts, heat generation and power consumption during operation, while still reducing or eliminating thrombosis or other damage to blood flowing through the pump.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure provides systems, devices and methods for supporting cardiac function, such as axial flow pumps. The intracardiac devices are particular useful for longer term implantation in patients that are, for example, suffering from congestive heart, for destination therapy (DT), bridge to transplant therapy (BTT) and for any patients with heart failure who are no longer responding to optimal medical management and are not candidates for heart transplant surgery. However, it will be recognized that the pumps described herein may also be used for shorter term “acute” use as, for example, mechanical circulatory support devices (MSC) to provide hemodynamic support to patients who present with cardiogenic shock and other disorders.

In one aspect, an axial flow pump configured for implantation into a human heart or vascular system comprises an elongate housing having first and second ends, an internal surface, a first inlet for blood disposed between the first and second ends and an outlet spaced longitudinally from the first inlet. The first inlet and the outlet define a primary blood flow path through the housing. The pump includes a rotatable element, such as a rotor, disposed within the housing and spaced from the internal surface to define a clearance therebetween. An impeller is coupled to the rotor for propelling blood from the first inlet to the outlet of the housing along the primary blood flow path. The housing includes a second inlet fluidly coupled to the clearance between the rotor and the housing to define a secondary flow path through the clearance. The blood passing through the secondary flow path continuously flushes the clearance between the rotor and the housing to minimize the formation and/or growth of blood clots and/or to remove heat generated by the rotor. This design, therefore, substantially reduces the risk of thrombosis within the pump or in the patient’s heart or vascular system.

In certain embodiments, the rotor and the impeller are suspended within the housing such that they are spaced from the inner surfaces of the housing. Thus, the secondary flow path also provides a fluid bearing for the rotor (and in some embodiments, the impeller). In certain embodiments, this fluid bearing is a hydrodynamic bearing. Reducing or eliminating contact surfaces and/or mechanical bearings between the rotating components of the pump and its housing reduces wear on these components, thereby increasing the longevity of the pump.

In certain embodiments, the rotor comprises at least one rotational element, such as a rib, vane, blade or other projection extending into the clearance between the rotor and the housing. The rib(s) are configured to draw blood into the secondary flow path during rotation of the rotor. The rib(s) may extend in a substantially helical or spiral direction around the rotor.

In other embodiments, the rotational element comprises at least one channel, groove, indentation, serration, notch, or the like extending around the outer surface of the rotor. The groove(s) draws blood into the secondary flow path during rotation of the rotor. In certain embodiments, the groove extends in a substantially helical or spiral direction around the outer surface of the rotor.

The pump may further comprise a motor stator within the housing for rotating the rotor to thereby drive the impeller. The motor stator may, for example, be located in the outer housing and may comprise stator windings that drive the rotor. Alternatively, the rotor may be driven with a motor that is coupled to the housing.

In another aspect, the pump is designed to create forces against the blood flowing through the secondary flow path that at least partially resist forces generated by the impeller and/or the rotor during pump operation to provide radial and/or axial stability to the pump. In certain embodiments, the secondary flow path is designed to provide axial stability to the rotor by at least partially resisting axial forces applied by the impeller and/or the rotor during operation of the pump. This hydrodynamic bearing reduces or completely eliminates the requirement for axial magnetic bearings to maintain the axial position of the rotor and impeller within the housing. This, in turn, reduces or eliminates the need for additional magnetic coils and associated electronics for such magnetic bearings, thereby providing a more compact axial pump with a reduced footprint within the heart chamber.

In one such embodiment, the second inlet is disposed at, or near, the first end of the housing and the outlet is disposed at, or near, the second end of the housing. Thus, the secondary flow path is in substantially the same axial direction as the primary flow path along the longitudinal axis of the housing. In this embodiment, the pump may further comprise a fluid pressure element in the secondary flow path that generates sufficient fluid pressure to create an axial force in the opposite direction as the force applied by the impeller, thereby at least partially resisting this axial force.

The fluid pressure element may comprise a fluid contacting surface or wall extending in a lateral direction relative to a direction of the secondary flow path or the longitudinal axis of the housing. This fluid contacting surface is positioned relative to the inner surface of the casing to create a region of higher fluid pressure for blood flowing through the secondary flow path. The surface is further disposed such that this region of higher fluid pressure generates a force against the fluid contacting surface in the opposite direction as the force applied by the impeller.

In some embodiments, the rotor comprises a substantially cylindrical outer surface and the fluid pressure element comprises an enlarged portion of the rotor having a larger diameter than the rotor. The enlarged portion comprises an angled surface extending from the cylindrical outer surface of the rotor in a lateral direction relative to a longitudinal axis of the housing. The angled surface is located on the opposite side of the enlarged portion from the impeller. In addition, the clearance between the angled surface and the inner surface of the housing has a smaller cross-sectional area than at least portions of the clearance between the outer surface of the rotor and the inner surface of the housing. This smaller cross-sectional area compresses the fluid within this region, increasing the fluid pressure and generating a force that is applied against the angled surface.

The enlarged portion of the rotor may be disposed between the rotor and the first end of the housing. Alternatively, this enlarged portion may be disposed between the rotor and the impeller, or between the rotor and the first inlet.

In certain embodiments, the secondary flow path is also designed to offset at least some of the radial forces applied to the rotor and/or impeller during operation. Thus, the secondary flow path also acts as a hydrodynamic radial bearing for the pump.

In one such embodiment, the rotor includes one or more variable pressure surfaces that create a variable fluid pressure at different locations on those surfaces. The variable pressure surfaces may each extend in a circumferential direction around the rotor such that a variable fluid pressure is created in this direction. In the event that the rotor moves closer to the inner surface of the housing, the variable pressure surfaces compress the blood flowing past them at the circumferential location that is closest to the inner surface of the housing to generate a force opposing this motion, thereby resisting the radial force that would destabilize the radial position of the rotor within the housing. Additional radial stability may also be provided by magnetic bearings, such as cooperating magnets in the housing and the pump components.

In one such embodiment, the rotor includes a helical groove extending around the outer surface and configured to draw blood into the secondary flow path during rotation of the rotor. The variable pressure surfaces comprise recessed portions of the outer surface of the rotor that extend from a first location adjacent the groove, where they have the largest cross-sectional area, circumferentially along the outer surface. to a second location, where the pressure surface is substantially parallel with the outer surface of the rotor (i.e., the pressure surface joins with the outer surface and is no longer recessed).

In other embodiments, the second inlet is disposed between the first and second ends of the housing. In these embodiments, the blood flowing through the secondary flow path is in substantially the opposite direction as the blood flowing in the primary flow path. In this embodiment, the force applied by the rotor against the blood in the secondary flow path is in the opposite direction as the force applied by the impeller to the blood in the primary blood path, thereby creating an offsetting force that at least partially resists the axial forces generated by the impeller.

The mass flow rate of the blood in the secondary flow path is substantially less than the mass flow rate of the blood in the primary flow path. This is because the primary function of the pump is to pump blood through the primary flow path from the left atrium to the aorta to assist cardiac function of the left ventricle. In a preferred embodiment, the mass flow rate of the blood in the secondary flow path is about 1% to about 20%, preferably about 5% to about 10%, of the mass flow rate of the blood in the primary flow path.

In another aspect, a method for supporting cardiac function in a patient comprises positioning an axial flow pump within a heart chamber and rotating an impeller within the pump to draw blood through a primary flow path such that the blood flows through an outlet of the pump and into the aorta. A rotor within the pump is rotated to draw blood into a second inlet of the pump through a secondary flow path between the rotor and the housing. The blood in the secondary flow path flushes clearance between the rotor and the housing to minimize the formation and/or growth of blood clots and/or to remove heat generated by the rotor.

In certain embodiments, the axial flow pump comprises a rotatable element, such as a rotor, with an external surface and one or more ribs extending from the external surface, or one or more channels extending into the external surface. Blood is drawn into the secondary flow path by rotating the rotor.

In certain embodiments, the housing includes an impeller coupled to the rotor. The impeller and rotor are suspended within the housing such that there is no contact therebetween.

In certain embodiments, the method further includes increasing fluid pressure within certain portions of the secondary flow path to at least partially offset axial and/or radial forces applied by the impeller and/or the rotor. In other embodiments, the method includes directing the blood flow through the secondary flow path in substantially the opposite direction as the primary flow path to at least partially offset axial forces applied by the impeller.

In one embodiment, the first inlet is fluidly coupled to the left atrium. The second inlet may be fluidly coupled to either the left or the right atrium. The secondary flow path may be in the same direction or the opposite direction as the primary flow path.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

DETAILED DESCRIPTION OF THE PREFERRED EMBODIMENTS

Figure 1:
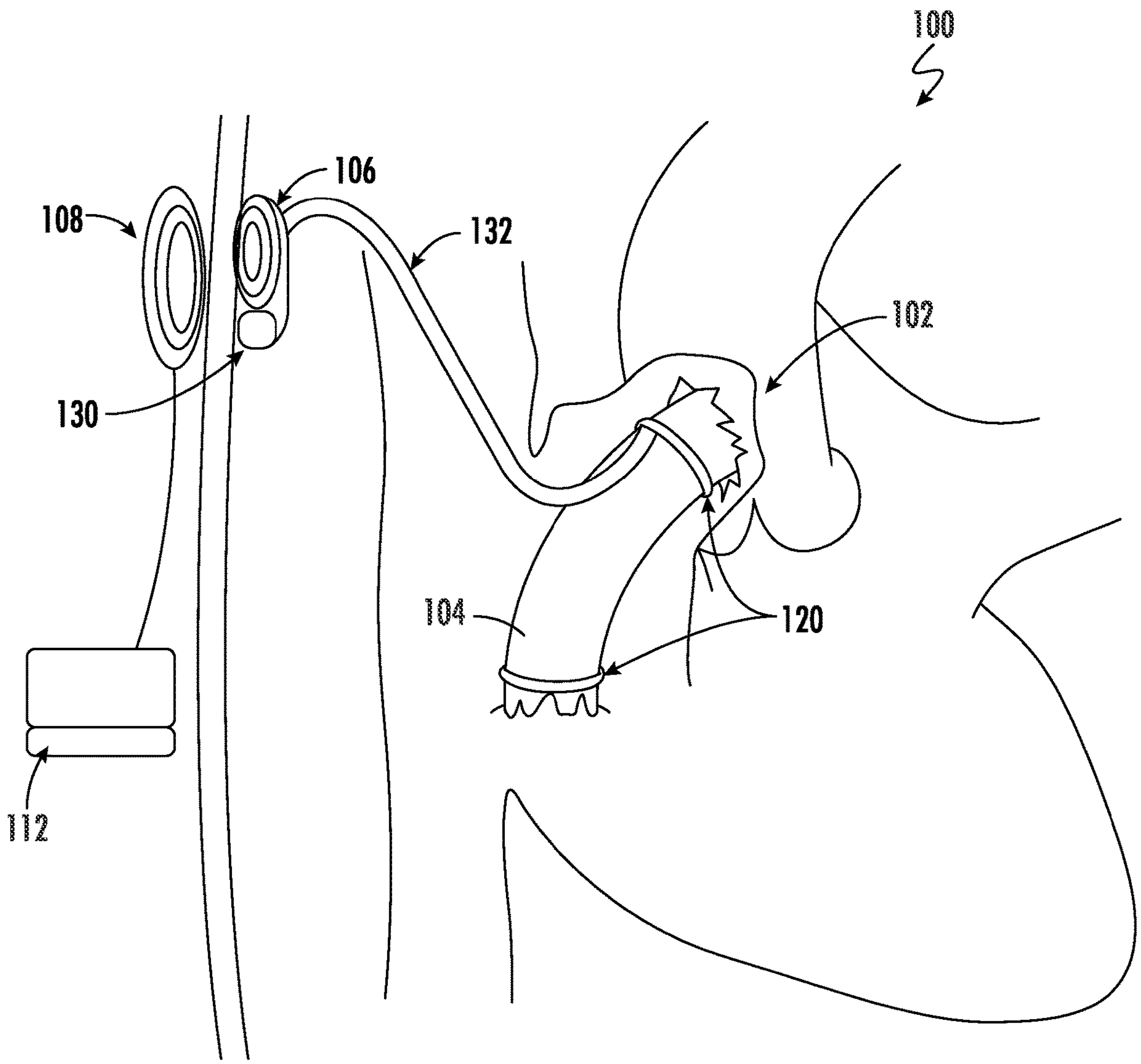
FIG. 1 is a schematic depicting an exemplary ventricular assist system.

Particular embodiments of the present disclosure are described hereinbelow with reference to the accompanying drawings; however, it is to be understood that the disclosed embodiments are merely exemplary of the disclosure and that the disclosure may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail. It should be understood also that the drawings are not drawn to scale and are not intended to represent absolute dimensions or relative size. Instead, the drawings help to illustrate the concepts described herein.

Systems, devices and methods are provided for supporting cardiac function. In the representative embodiments, the devices are implantable intracardiac devices, such a ventricular assist devices (VADs) for assisting or replacing cardiac function, such as in the case of ventricular failure. The intracardiac devices are particular useful for longer term implantation in patients suffering from congestive heart failure, for destination therapy (DT), bridge to transplant therapy (BTT) and for any patients with heart failure who are no longer responding to optimal medical management and are not candidates for heart transplant surgery. However, it will be recognized that the devices of the present disclosure may also be used in more acute applications, such as mechanical circulatory support devices (MSC) to provide hemodynamic support to patients who present with, for example, cardiogenic shock. In addition, the intracardiac devices may be used in other applications, such as artificial hearts, ECMO devices, implantable heart monitors and defibrillators, pacemakers, or other intracardiac devices.

In the representative embodiments, the intracardiac devices may include an axial flow pump designed to support cardiac function by pumping blood from the left atrium to the patient's arterial system. The pump is housed within a casing that may, or may not, have a collapsible stent design depending on the method of implantation. The pump may be wirelessly powered and controlled. In some embodiments, the pump may be implanted using minimally invasive procedures without the need for open heart surgery.

In certain cases, the intracardiac device may include inflow and outflow valves that are closeable to seal the pump from a subject's anatomy. Closing the inflow and outflow valves modulate flow and allow for sealing of the pump, prolonging the life of the pump when not in use.

In some embodiments, the intracardiac devices may include a cleaning system configured to introduce and circulate cleaning solutions and therapeutics to the pump. For example, the cleaning system includes an access port and a pump that enables the introduction and rapid circulation of a cleaning solution into the pump. Coupling the cleaning system to the inflow and outflow valves allows for maintenance of the pump while implanted without biological or chemical fouling (such as thrombosis, intimal hyperplasia, encrustation, and the like).

Referring now to FIG. 1, an exemplary ventricular assist system 100 includes an intracardiac device 102 that is implanted into a heart chamber. Intracardiac device 102 comprises an outer casing 104, which in some embodiments may comprise a substantially cylindrical stent body. Casing or stent 104 includes an internal lumen running between two open ends and a pump, such as an axial pump, (not shown) between the two open ends. Stent 104 can have a mesh or wire construction, such that stent 104 can be collapsible into a narrow configuration to facilitate insertion and expandable at a site of implantation. In certain embodiments, stent 104 comprises a covering, which can have a biological (such as pericardium or engineered tissue scaffold), artificial (such as a polymer), or a biological and artificial hybrid construction.

Figure 2:
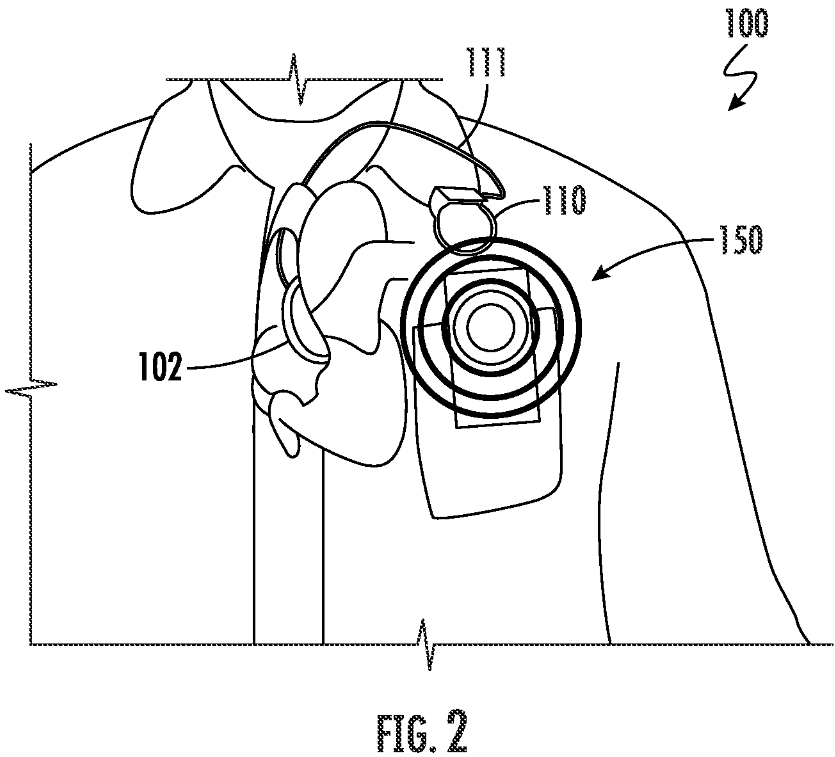
FIG. 2 illustrates an exemplary VAD implanted within a patient with a wireless power source.
Figure 3:
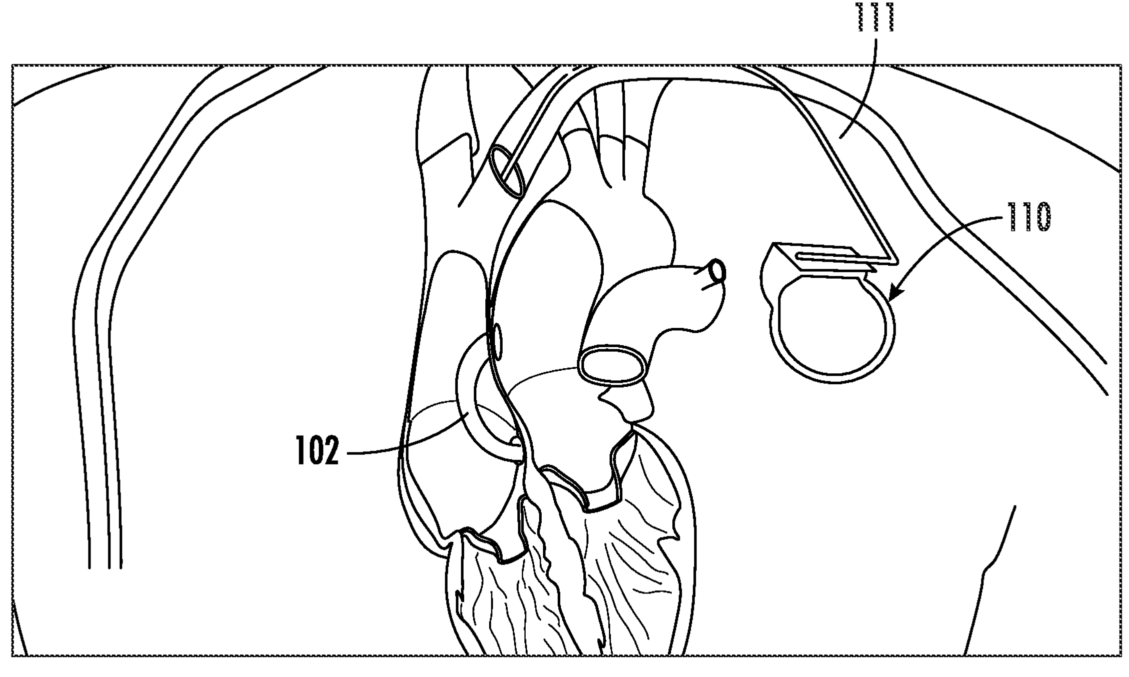
FIG. 3 illustrates the implanted portions of the VAD of FIG. 2.

In some embodiments, stent 104 may include a valve 120 positioned at each open end and a cleaning system 130 fluidly connected to device 102 via a lumen 132. The various components of device 102, including each valve 130, the axial pump, and cleaning system 130, can be powered by a receiving coil 106 wirelessly receiving electromagnetic energy from a transmitting coil 108 and a battery (discussed in further detail below). Coil 106 and/or cleaning system 130 may be housed within an internal controller 110 that is implanted within the patient (see FIG. 2). In certain embodiments, device 102 further comprises an external controller 112 configured to communicate with the wireless transmitter 108 to activate and modulate each of the components of device 102 (discussed in more detail below). For example, external controller 112 can be configured to wirelessly open and close each valve 120, to activate and modulate the speed of the axial pump, and to activate cleaning system 130. A more complete description of suitable intracardiac devices can be found in International Publication No. WO 2019/241556, U.S. Pat. No. 9,919,088, the complete disclosures of which are incorporated herein by reference in their entirety for all purposes.

FIGS. 2-5 illustrate the representative intracardiac system 100 implanted in a patient. As shown, device 102 is coupled via a suitable connector 111 to controller 110, which may be implanted subcutaneously in any suitable location known to those of skill in the art. Controller 110 includes wireless electronics, receiving coil 106 and a power source, such as a battery. System 100 may further include a wireless power transmitter 150 that includes transmitting coil 108 to communicate power and data to controller 110. Power transmitter 150 also may wirelessly communicate information to external patient and clinician devices to enable continuous and remote patient and system monitoring. A more complete description of suitable wireless power systems can be found in U.S. Pat. No. 9,415,149, the complete disclosure of which is incorporated herein by reference in its entirety for all purposes Of course, it will be recognized that the systems and methods of the present disclosure may be used with other intracardiac systems. For example, power transmitter 150 may be directly coupled to controller 110, or they may both be incorporated into the same device. This device may be implanted subcutaneously within the patient, or it may be implanted within the patient's heart. Alternatively, the power transmitter and controller may be incorporated into intracardiac device 102.

Intracardiac device 102 may be implanted into a heart chamber through open surgical procedures, percutaneously, endoscopically, or through a minimally invasive procedure, for example, by advancing a catheter through the patient's vascular system. The device 102 may be inserted through a puncture in the cardiac wall and introduced into the heart such that casing 104 sealingly closes the puncture hole while device 102 is in the interior of the heart and a cannula or outlet tube coupled to device 102 is outside the heart.

In one minimally invasive procedure, casing 104 is in the form of a collapsible stent (or "graft") that is implanted into the right atrium, the superior vena cava (SVC) and/or the inferior vena cava (IVC) of the patient's heart. An arterial catheter is advanced through the ascending aorta into the SVC and then through the right atrium into the left atrium. The anchors may be deployed at the atrial septum and the SVC. The catheter is then withdrawn from the right atrium to deploy the graft between the anchors.

In another minimally invasive procedure, a catheter is advanced through a blood vessel of the patient to deliver device 102 into a heart chamber, such as the right atrium. The intracardiac device 102 is then advanced through a femoral vein into the heart chamber and implanted therein. Delivering the intracardiac device into the heart chamber through the vein allows for use of a larger bore catheter due to the larger size and compliance of veins, thereby minimizing stress on the femoral artery or aortic arch and reducing internal bleeding, bruising and other potential complications associated with a purely arterial approach.

In one such embodiment, the intracardiac device is advanced through an entry port and through the femoral vein and then coupled to the arterial catheter within the femoral vein the inferior vena cava (IVC) or the heart chamber (e.g., via transcaval manipulation of the arterial catheter). The arterial catheter is then withdrawn into the heart chamber to advance the intracardiac device into the heart chamber. In this "in vivo" approach, the device is coupled to the catheter within the patient's body.

In an exemplary embodiment of the "in vivo" approach, a guidewire or similar device is advanced through the femoral vein into the IVC or the right atrium of the patient's heart. The venous guidewire is then coupled to a guidewire in the arterial catheter via a snare or similar device and the arterial guidewire is withdrawn through the femoral vein. The arterial catheter guidewire is then coupled to the intracardiac device and retracted back into the right atrium with the device. The device is then withdrawn into the arterial catheter with the guide wire and implanted within the heart chamber.

In another embodiment, the arterial catheter is advanced from the heart chamber through the femoral vein to an exit portal of the femoral vein. The intracardiac device is then coupled to the catheter externally of the patient's body and the catheter is withdrawn back through the femoral vein into the heart chamber to advance the intracardiac device into the heart chamber. In this "ex vivo" approach, the device is coupled to the catheter outside of the patient's body.

In an exemplary embodiment of the "ex vivo" approach, the intracardiac device is manually positioned within the arterial catheter exterior to the patient's body. The arterial catheter is then withdrawn back through the femoral vein into the heart chamber and the device is implanted therein.

In both the "in vivo" and "ex vivo" embodiments, the intracardiac device is positioned within the arterial catheter by moving the distal end portion of the arterial catheter from a collapsed position, where it is sized for advancement through an artery, to an expanded position, where it is sized to receive the intracardiac device. In certain embodiments, the arterial catheter is expanded while maintaining its steerability within the vasculature of the patient. A more complete description of suitable methods for implanting device 102 into the right atrium can be found in U.S. Provisional Patent Application Ser. No. 63/217,388 filed Jul. 13, 2021, the complete disclosure of which is incorporated herein by reference in its entirely for all purposes.

Figure 4:
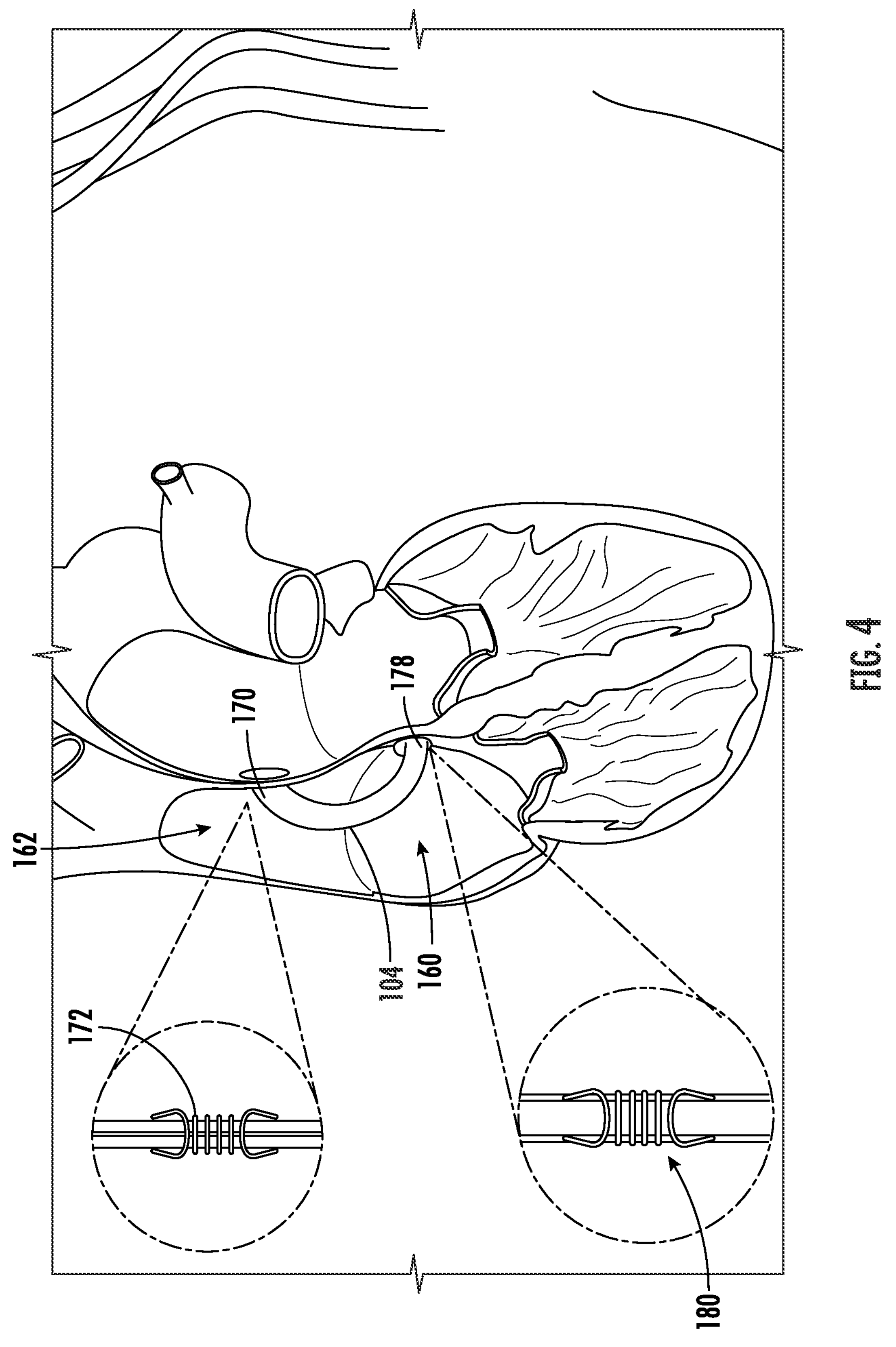
FIG. 4 illustrates a stent of the VAD of FIG. 2 with first and second anchors for securing the VAD in the right atrium of a patient's heart.
Figure 5:
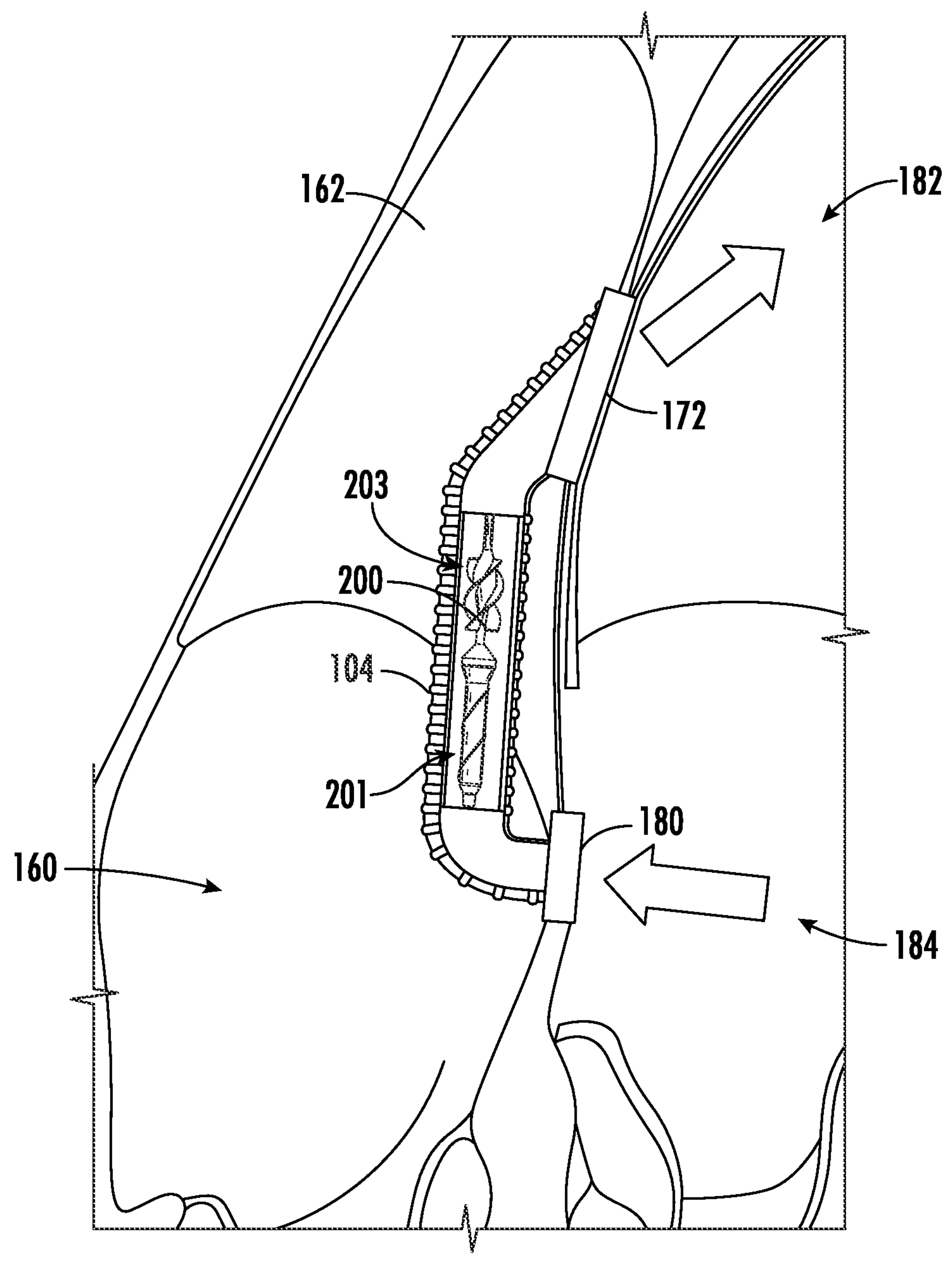
FIG. 5 is a cross-sectional view of a stent implanted in the right atrium.

FIGS. 4 and 5 illustrate a representative stent 104 implanted within the right atrium 160 (or right atrium appendage) and the SVC 162 of a patient. As shown, stent 104 includes a first end 170 coupled to a first anchor 172 and a second end 178 coupled to a second anchor 180. First anchor 172 is preferably positioned such that first end 170 of stent 104 outflows into the aorta 182 and second anchor 180 is positioned such that second end 178 receives inflow from the left atrium 184. The axial pump 200, which includes a motor 201 and an impeller 203 (discussed in detail below) is housed within stent 104 between first and second ends 170, 178 to pump blood from the left atrium 184 into the aorta 182 and throughout the patient's body. Thus, the pump essentially bypasses the left ventricle by drawing freshly oxygenated blood from the left atrium 184 and propelling this blood into aorta 182, thereby reducing the pre-load on the left ventricle.

Since device 200 is implanted in the right atrium 160, any blood clots that form on the pump will remain in the right atrium 160 and will not break away and pass into the aorta 182 and the arteries supplying blood to the brain, thereby eliminating the potential for a thrombotic stroke. In addition, the internal pressure within the right atrium is lower than any other chamber of the heart, which decreases the stresses and loads on the blood pump, thereby reducing bleeding events, mechanical failure and/or wear on the pump components over time.

Since there are no valves between the right atrium 160 and the SVC 162 or the inferior vena cava (IVC), at least a portion of device 200 may extend from the right atrium 160 and into the SVC 162. This provides a larger combined space for device 200 and allows device to be longer than it otherwise would be, if, for example, it were implanted in the left atrium or the left ventricle. This additional length allows for the design of a more efficient pump. In addition, since the SVC 162 extends alongside the aorta 182, there are multiple locations along the SVC 162 in which to create an anastomosis for passing the anchor 172 therethrough.

In certain embodiments, anchors 172, 180 are coupled to, or integral with, stent 104 prior to deployment of stent 104 into the patient's heart. In these embodiments, stent 104 and anchors 172, 180 are advanced together through the femoral vein and into the right atrium. In other embodiments, anchors 172, 180 are separate from stent 104. In these embodiments, anchors 172, 180 are configured for deployment through the vascular system such that anchors 172, 180 may be secured to suitable locations within the patient's heart. Stent 104 may be coupled to anchors 172, 180 in vivo after they have been secured to such locations in the heart. In yet another embodiment, one of the anchors is secured to, or integral with, stent 104 prior to deployment of stent 104 within the heart. In this embodiment, the other anchor is secured within the heart, and then stent 104 and the anchor are advanced into the right atrium together. Stent 104 is coupled to the anchor that is already secured to the heart, and the other anchor is secured to complete deployment of stent 104.

Figure 6:
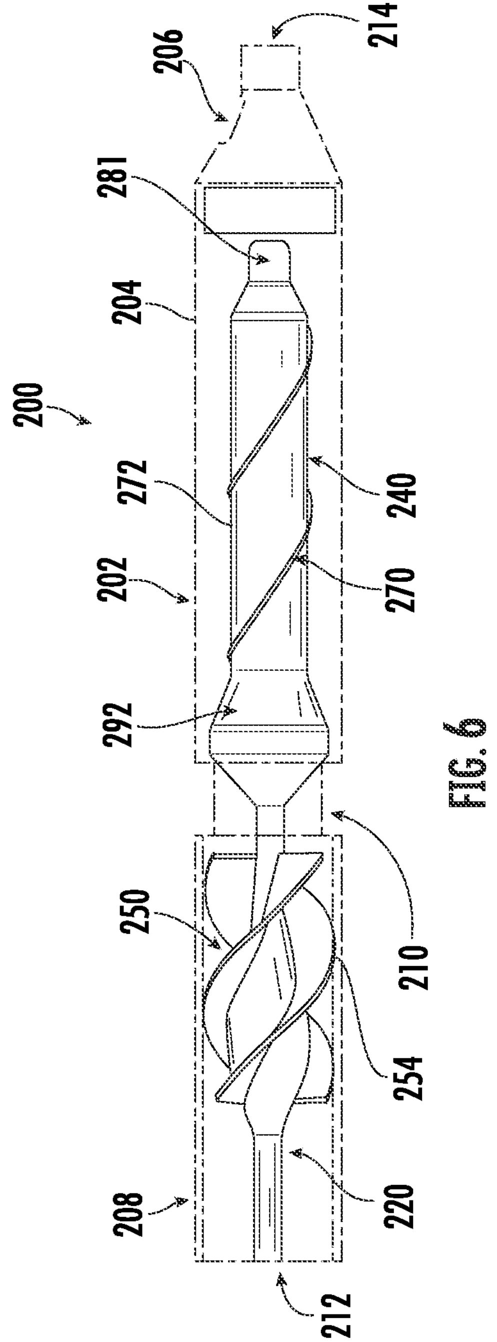
FIG. 6 is a side view of an axial flow pump.

Referring now to FIGS. 6-8, an exemplary embodiment of an intracardiac device 200 includes an outer casing 202 having a substantially cylindrical main body 204 with first and second ends 206, 208. Main body 204 preferably has a substantially uniform outer diameter to facilitate insertion of device 200 into an artery or specific delivery device. In some embodiments, however, device 200 may be inserted percutaneously, endoscopically or through an open incision in the patient. In these embodiments, device 200 may have other configurations.

Main body 204 includes a first inlet 210 located between first and second ends 206, 208, an outlet 212 at, or near, second end 208 and a second inlet 214 at, or near, first end 206. First inlet 210 and outlet 212 are fluidly coupled to each other to define a primary blood flow path 220 through an internal lumen in casing 202. Second inlet 214 is fluidly coupled to either or both of first inlet 210 and outlet 212 to define a secondary blood flow path 230 through an internal lumen of casing 202, as discussed in more detail below.

First inlet 210 preferably comprises a semi-circular opening in outer casing 202 that extends at least partially around the circumference of casing 202, preferably at least about 25% of the circumference, and more preferably at least about 50%. The exact size and shape of first inlet 210 is designed to provide sufficient flow from a heart chamber surrounding device 200 into primary blood flow path 220. Of course, other configurations are possible. For example, first inlet 212 may comprise one or more openings spaced from each other around the circumference of casing 202. Such openings may have any suitable cross-sectional shape, e.g., circular, square, diamond, rectangular, triangular or the like.

Figure 8A:
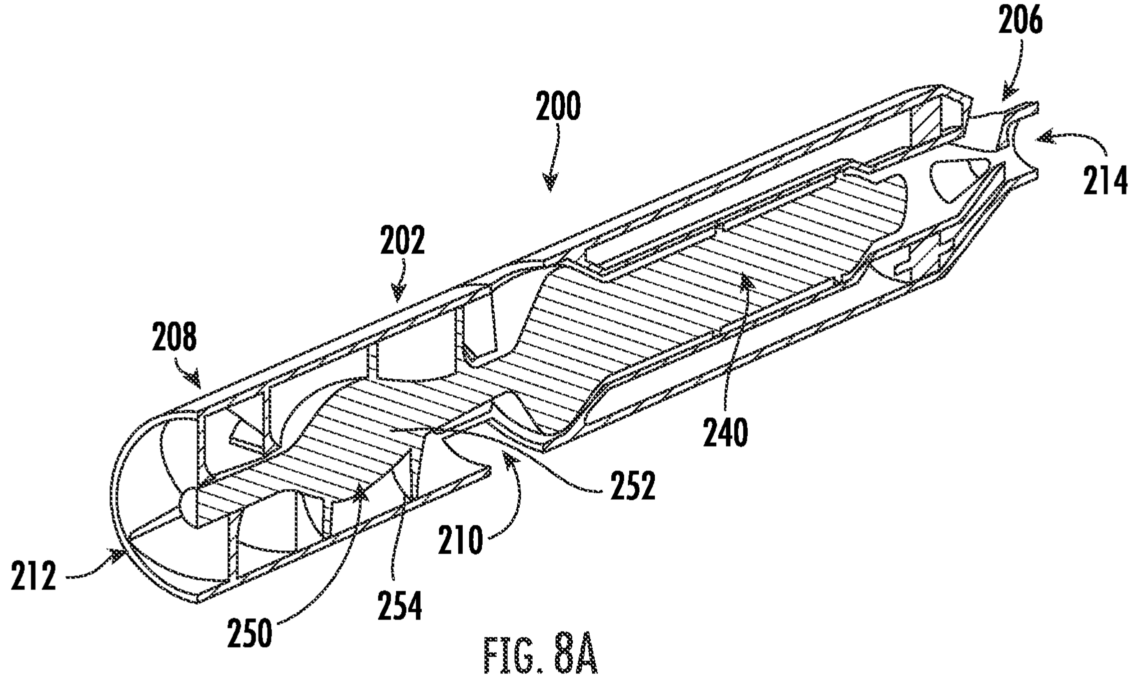
FIG. 8A is another cross-sectional view of the pump of FIG. 6.
Figure 8B:
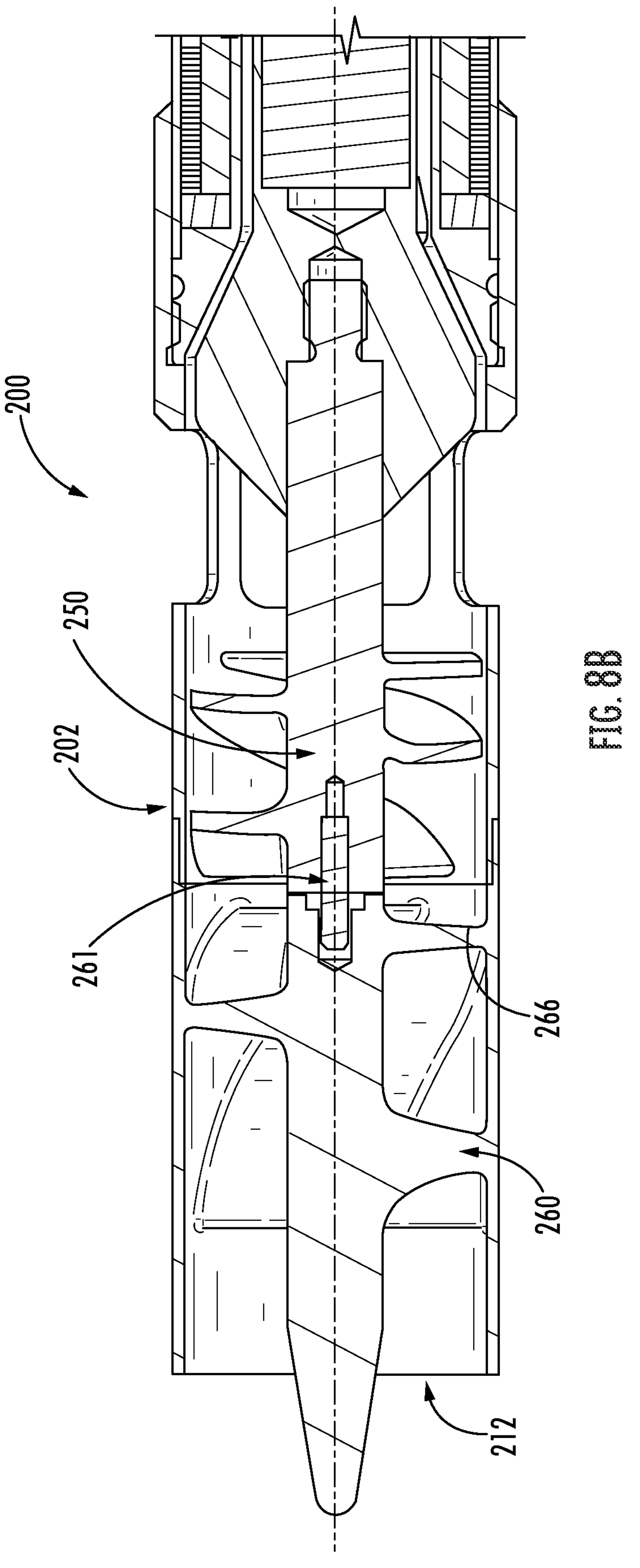
FIG. 8B is an enlarged cross-sectional view of a pumping section of the pump of FIG. 6.
Figure 8C:
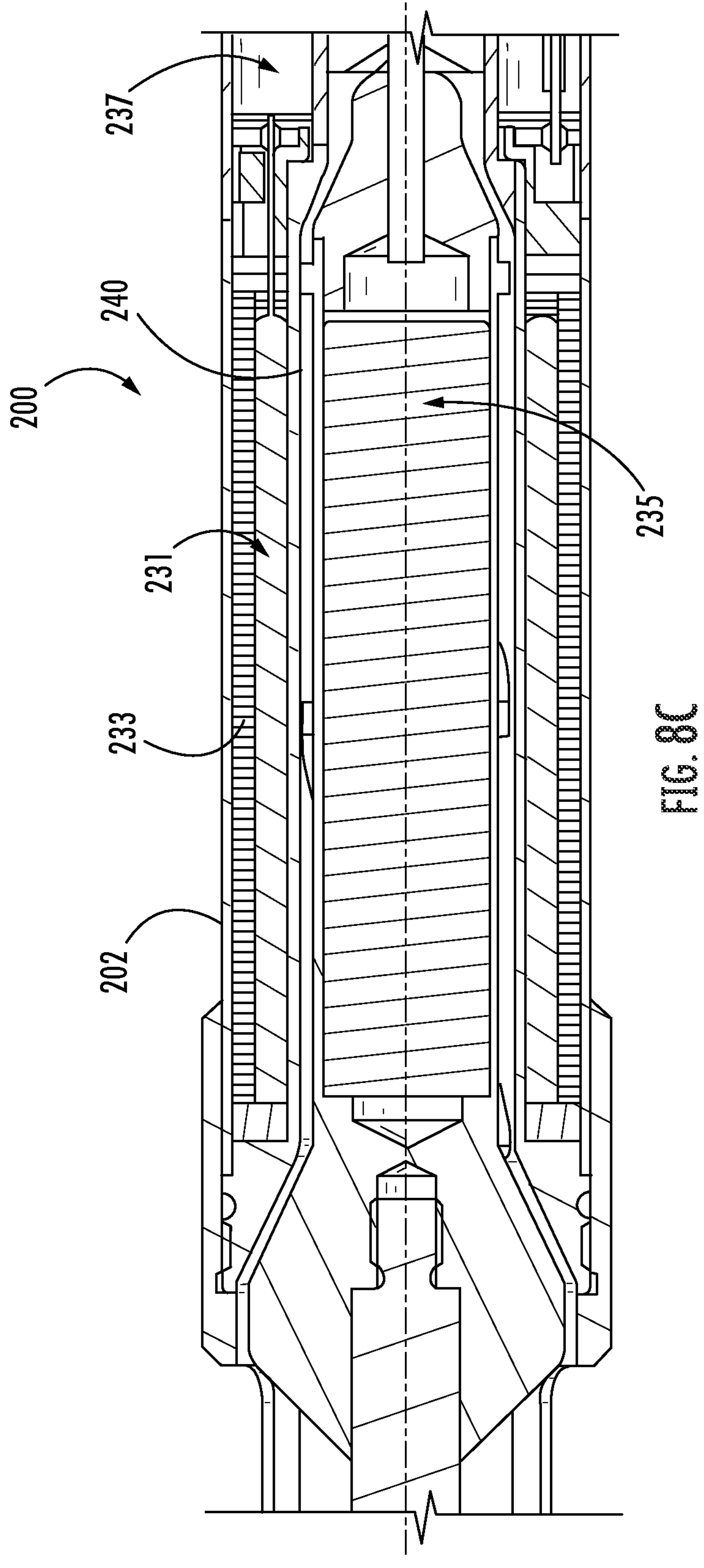
FIG. 8C is an enlarged cross-sectional view of a motor body section of the pump of FIG. 6.

As shown in FIG. 8C, device 200 further includes a motor 231 that is preferably integral with outer casing 202 and may include stator windings 233, a motor core 235 and a motor controller 237. A tubular rotatable element 240 is positioned within casing 202 between first and second inlets 210, 214. Rotatable element 240 comprises a rotor portion of the motor 231 and is configured to be rotated (i.e., driven) by the motor stator or windings 233. In one embodiment, the motor 231 includes one or more permanent magnets and rotor 240 includes one or more magnets such that rotor 240 may be rotated around its longitudinal axis by a suitable magnetic field, as is known in the art. Casing 204 may be formed from a magnetically permeable material selected to minimize power losses due to magnetic hysteresis. Electrical conductors 239 passing through casing 202 and an external cable 241 provide power and control signals to motor controller 237 (see FIG. 8D). In certain embodiments, device 200 may include a tensile relief 243 between cable 241 and casing 202 to relief the stress or strain applied against cable 241 when the motor is operating.

Rotor 240 is coupled to an impeller 250 that comprises a hub 252 and one or more rotating blades 254 that project from hub 252 for drawing blood through inlet 210. The blades 254 may take any appropriate shape and be of any appropriate number. Blades 254 preferably define a clearance with the inner surface of casing of about 0.1 mm to about 0.8 mm, preferably about 0.2 mm to about 0.4 mm, more preferably about 0.3 mm. In one embodiment, blades 254 have a substantially helical shape such that the blades 254 spiral around hub 252 from the upstream end to the downstream end. Blades 254 may have the same, or a different, pitch. Each blade 254 may have a pitch that varies from hub 252 to the tip of the blade 254.

Figure 7A:
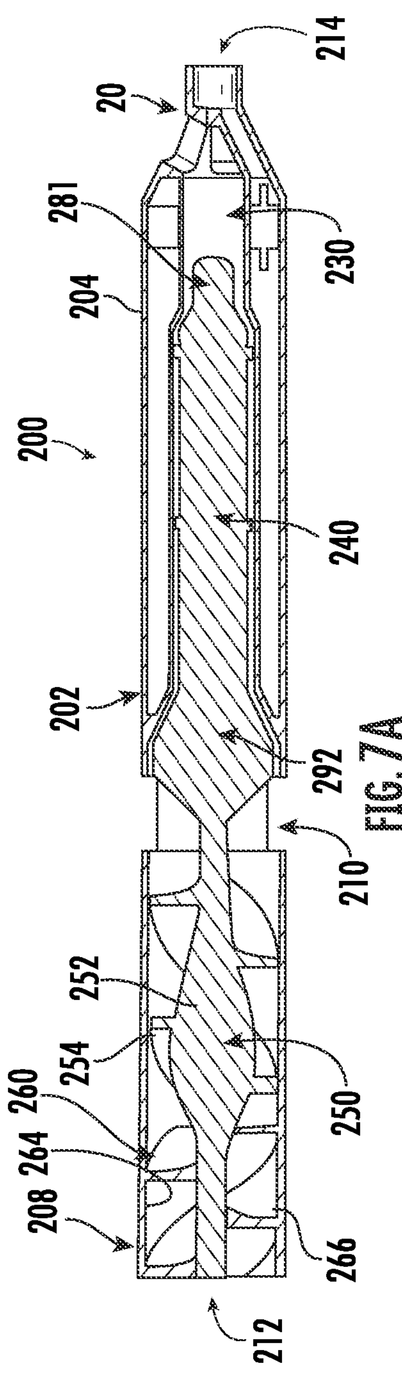
FIG. 7A is a cross-sectional view of the axial flow pump of FIG. 6.
Figure 7B:
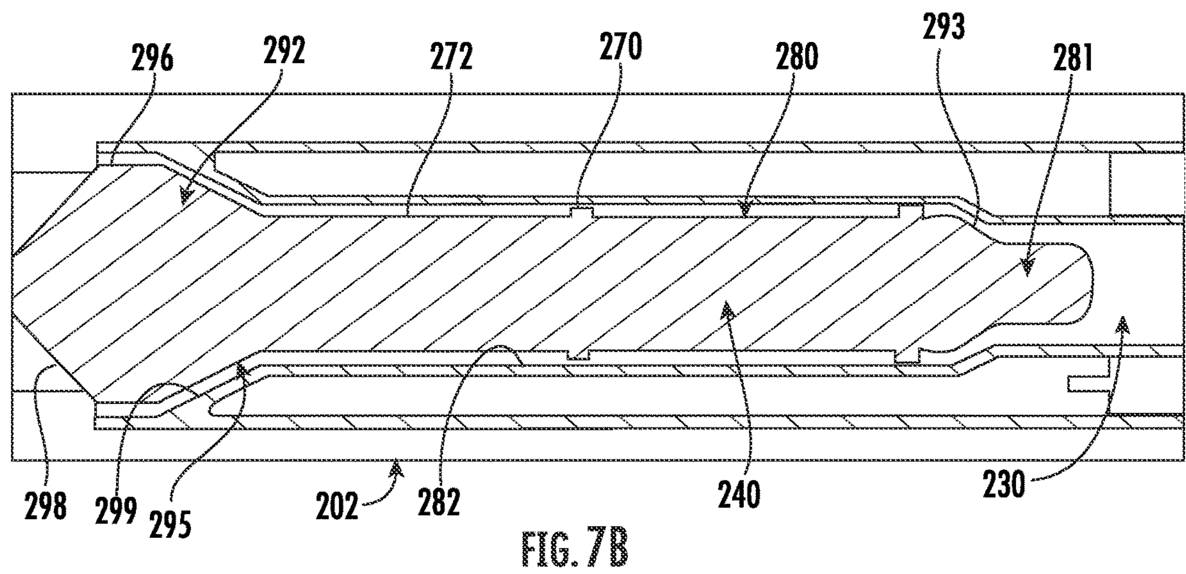
FIG. 7B is an enlarged cross-sectional view of a rotor of the axial flow pump.
Figure 7C:
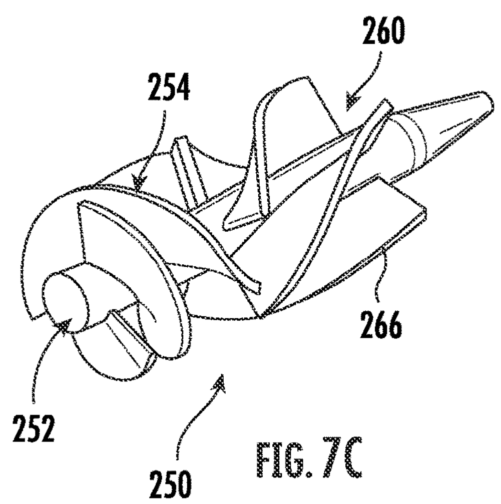
FIG. 7C is an enlarged perspective view of an impeller of the axial flow pump.

As shown in FIG. 7C, impeller 250 may include three blades 254 extending from hub 252 and spaced apart from each other. In certain embodiments, the pitch angle of each of the blades 254 changes in the longitudinal direction such that the angle between the blade surface and the blood flow increases in the downstream direction. Thus, the angle between the blade surface at the hub (where the blood first contacts the blade) is smaller and closer to parallel to the blood flow direction to reduce turbulence and minimize damage to the blood cells upon initial contact with blade 254. As the blood flows along the surface of the blade downstream, this angle increases to provide sufficient power to accelerate the blood flow and propel the blood radially relative to the housing.

Impeller further comprises a stator 260 that is configured to redirect the flow of the blood from the radial direction to the longitudinal direction towards outlet 212. Stator 260 includes one or more blade-shaped surfaces 266 that have pitch angles that decrease in the downstream direction. Similar to the impeller blades, surfaces 266 are designed to reduce the impact of the radial blood flow at the upstream end of the surface 266 and then to gradually redirect this blood flow in the longitudinal direction. This design reduces turbulence and minimizes damage to blood cells. Stator 260 may be coupled to impeller 250 with a mechanical bearing 261 (see FIG. 8B) or other suitable coupling device.

Rotor 240 preferably includes one or more ribs 270 extending from an outer surface 272 of rotor 240. Ribs 270 may comprise blades, vanes or other projections that extend around outer surface 272 and are configured to draw fluid into casing from second inlet 214 as rotor 240 rotates around its longitudinal axis. Ribs 270 preferably have a substantially helical shape with the same orientation as impeller blades 254 such that the flow of blood in secondary blood flow path 230 is in substantially the same direction as primary blood flow path 220.

Device 200 provides an efficient design that may pump at least 5 Liters of blood per minute, preferably at least about 6 Liters/minute, at the physiological pressures typically existing within the heart chambers. Applicant has conducted tests of the pump in device 200 to measure the pump's performance parameters. These tests have shown that the pump can pump over 5.5 Liters/minute of water at pressures around 59 mmHG at a rotational speed of about 25.4K RPM, and over 6 Liters/minute (about 6.4 Liters/minute) at pressures around 85 mmHG at a rotational speed of about 27.6K RPM. In other tests, the pump has pumped about 5.06 Liters/minute of water at pressures around 71.12 mmHG at a rotational speed of about 22K RPM, about 4.99 L/m of water at pressure around 99.55 mmHG at rotational speed of about 25K RPM and about 5.06 L/m of water at pressure around 121.56 mmHG at a rotational speed od about 27K RPM.

In addition, the pump consumes less power than conventional axial flow pumps. Applicant has tested the power consumption of pump 600 in water and has determined that the pump consumes about 27.07 Watts at 22K RPM, about 33.57 Watts at 25K RPM and about 36.67 Watts at 27K RPM. Accordingly, Applicant has tested the pump described above and determined that this pump has increased pressure at the tested rotational speeds, a higher flow rate at peak pump efficiency and a decreased power consumption at the tested speeds.

Of course, the pumps described herein are not limited to the specific impeller configuration described above and shown in the figures. For example, pump 200 can alternatively employ a fluid actuator that has a shaftless design for the actuation of fluids. The actuator comprises a housing having a plurality of blades. The housing has a hollow, substantially cylindrical shape having a long axis with open ends and an outer and an inner surface. Each of the blades is attached to the inner surface of the housing and extends from opposite ends of housing in a helical pattern. The blades are thereby configured to actuate a fluid by the rotation of the housing along its long axis. The rotation can be achieved by mechanical linkage with a motor, such as by a rim driven connection or an end-driven connection. The rotation can also be achieved by magnetic coupling with external electromagnets or a rotating magnet. The blades may have any suitable cross-section shape, including a substantially parallelogram-like cross-sectional, rectangular, with rounded edges, with sharp edges, and the like. A more complete description of a suitable fluid actuator with a shaftless design can be found in International Patent Application No. PCT/US2019/037047, the complete disclosure of which is incorporated herein by reference in its entirety for all purposes.

As shown in FIG. 7B, rotor 240 defines a clearance 280 between its outer surface 272 and the inner surface 282 of casing 202. This clearance 280 provides the space for secondary blood flow path 230. Blood flowing through secondary flow path 230 supports rotor 240 within casing 202, thereby providing a fluid bearing for rotor 240 (i.e., with no mechanical bearings). In addition, the blood continuously flushes clearance 280 to minimize the formation and/or growth of blood clots and/or to remove heat generated by the motor and rotor 240. The width of clearance preferably remains substantially constant and is in the range of about 0.1 mm to about 0.8 mm, preferably about 0.2 mm to 0.4 mm, and more preferably about 0.3 mm. This width is preferably substantially the same as the clearance between impeller blades 254 and casing 202.

The operation of rotor 240 and impeller 250 creates a force that draws these element forward (i.e., in the direction opposite the blood flow or left to right in FIG. 6). Since device 200 does not contain any mechanical bearings to arrest this movement and prevent the rotor 240 from being drawn so far forward that it contacts the inner surface of casing 202, device 200 includes one or more fluid pressure elements that provides resistance to the flow of blood along secondary flow path 230. This resistance at least partially offsets these axial forces and serves to arrest the forward translation of rotor 240 and impeller 250 within casing 202.

In one embodiment, the fluid pressure elements comprises an enlarged bulb 292 coupled to, or integral with, rotor 240 and having an outer diameter larger than the outer diameter of rotor 240. Bulb 292 includes an outer surface 296, a first inclined surface 294 adjacent the outer surface of rotor 240 that is transverse to the flow of blood in secondary flow path 230 and a second inclined surface 298 adjacent inlet 210. Outer casing 202 includes a substantially cylindrical inner surface 282 that surrounds rotor 240 to provide clearance 280. This inner surface 282 includes an inclined portion 299 that extends alongside inclined surface 294 of bulb 292 to form a clearance 295 therebetween.

Clearance 295 has a smaller cross-sectional area than clearance 280. Thus, fluid flowing clearance 295 is compressed creating a higher fluid pressure within this area. This higher fluid pressure applies a force against inclined surface 294 of bulb 292. The force applied against bulb 292 is in the opposite direction of forces applied by impeller 250 and rotor 240 and therefore at least partially resists these axial forces to maintain the axial position of impeller 250 and rotor 240 relative to housing.

The angle of inclined surface 298 is critical. The larger the angle between inclined surface 298 and the longitudinal axis or the direction of clearance 280, the greater the force that is applied against inclined surface 298 as blood flows therethrough (the relative cross-sectional area of clearance 295 will almost impact these forces). On the other hand, a large change in direction of blood flow through clearance 295 could cause damage to the blood cells. Therefore, Applicant has discovered that the optimal angle for inclined surface is about 5 degrees to about 45 degrees, preferably between about 10 degrees and about 30 degrees.

Of course, it will be recognized that other configurations for providing an offsetting axial force may be included in device 200. For example, the thickness of clearance 280 may be reduced in others places along secondary flow path 230 to create high pressure regions. Alternatively, secondary flow path 230 may include other surfaces or elements, such as projections extending into path 230 from either rotor 240 or casing 204, or a roughened surface on the rotor or casing. In some cases, secondary flow path 230 may be designed to provide a non-linear path through casing 204 to provide additional force vectors in the opposite direction of the flow provided by impeller 250.

Device 600 may further include an additional magnetic bearing to maintain the axial positions of rotor 240 and impeller 250 in the event that the secondary flow path does not sufficiently resist these forces. In one embodiment, for example, the axial magnetic bearing may comprise a permanent axial housing magnet (not shown) positioning within casing 202 that cooperates with a permanent axial rotor magnet (not shown) positioned in the rotor 240 and/or the impeller 250. In another embodiment, the axial magnetic bearing may include an active magnetic bearing that operates alone or in conjunction with a passive magnetic bearing. In this embodiment, the axial magnetic bearing may comprise, for example, a cylindrical passive magnet designed to counteract the axial forces encountered when rotor 240 is up to speed, surrounded by an active magnet, designed to compensate for additional axial loads, such as those present during pre-load or after-load of impeller 250. In yet another embodiment, permanent magnets may be radially distributed around impeller 250 and/or rotor 240. The attractive force of the magnetic coupling provides axial restraint to impeller 250.

Device may also include a radial magnetic bearing for stabilizing radial forces against rotor 240 and impeller 250 to minimize contact between these components and casing 202. For example, permanent radial bearing magnets (not shown) may be disposed within casing 202 and designed to cooperate with rotor bearing magnets in rotor 240 and/or impeller 250. The radial bearing magnets allow the rotor 240 and impeller 250 to rotate relative to casing 202 without significant radial contact. In addition, they assist the fluid bearing described above to maintain the annular clearance 280 between rotor 240 and casing 202, as well as the clearance between impeller blades 254 and casing 202.

Rotor 240 may further include an upstream enlarged hub 281 positioned at the end of rotor 240 opposite impeller 250 that includes one or more magnets therein (not shown) to form the axial and/or radial magnetic bearings for device 200.

Alternatively, hub 281 may function similar to enlarged portion 292 of rotor 240 to provide a relatively high fluid pressure region that creates stabilizing axial forces. For example, hub 281 is designed with a smaller outer diameter than the remainder of rotor 240 (see FIG. 7B). In this configuration, hub 281 and rotor 240 define an inclined surface 293 therebetween. Inclined surface 293 may be configured to create a clearance between hub 281 and the inner surface of housing 202 that has a smaller cross-sectional area than the cross-sectional area of clearance 280. Similar to the above description of enlarged portion 292, this increases the fluid pressure within this clearance and applies a force against inclined surface 293.

Figure 7D:
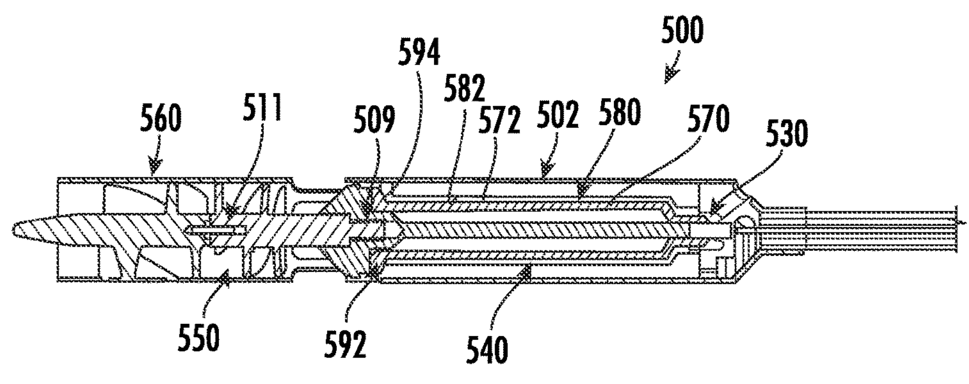
FIG. 7D is a side cross-sectional view of another embodiment of an axial flow pump.
Figure 7E:
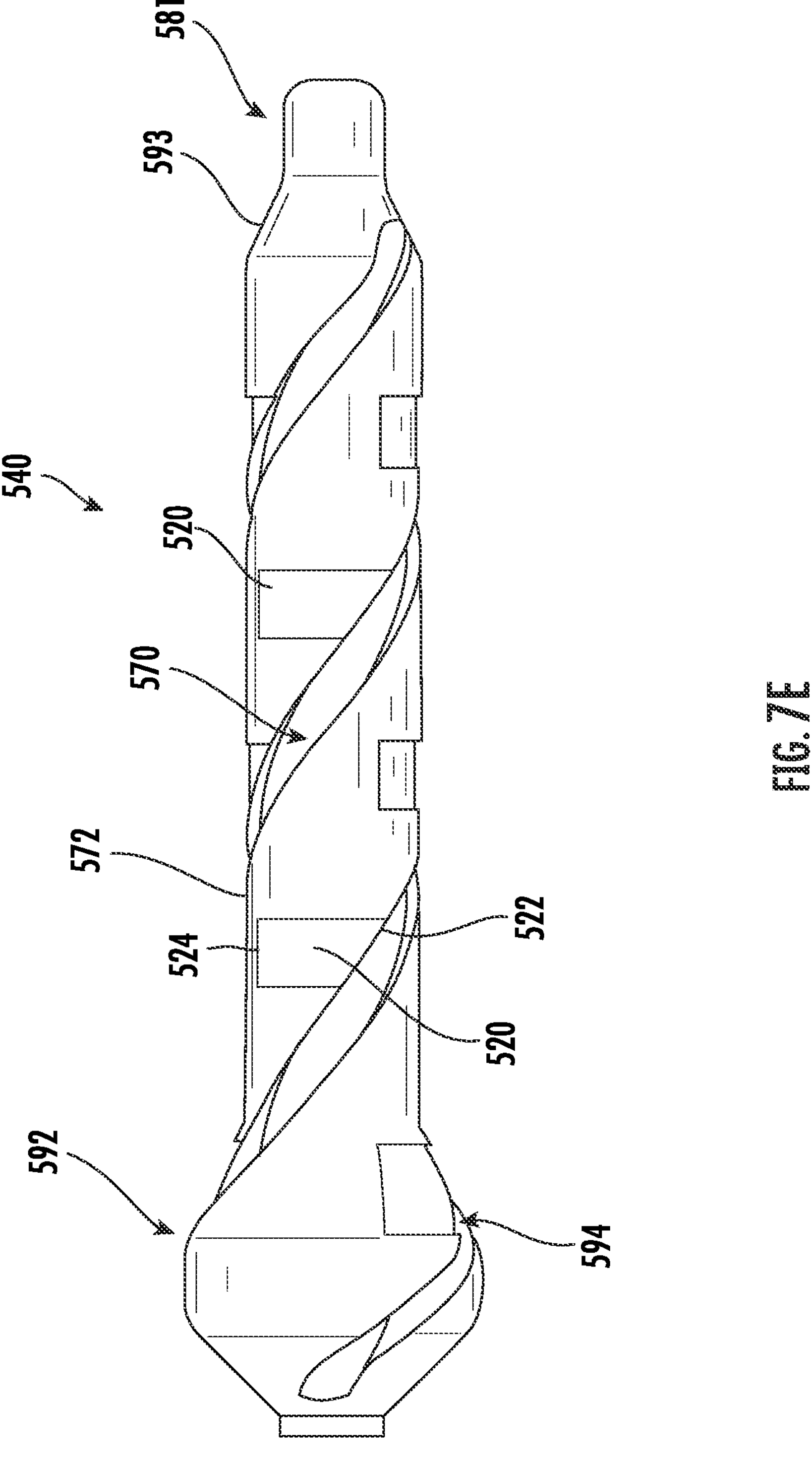
FIG. 7E is a perspective view of a rotor for the axial flow pump of FIG. 7D.
Figure 7F:
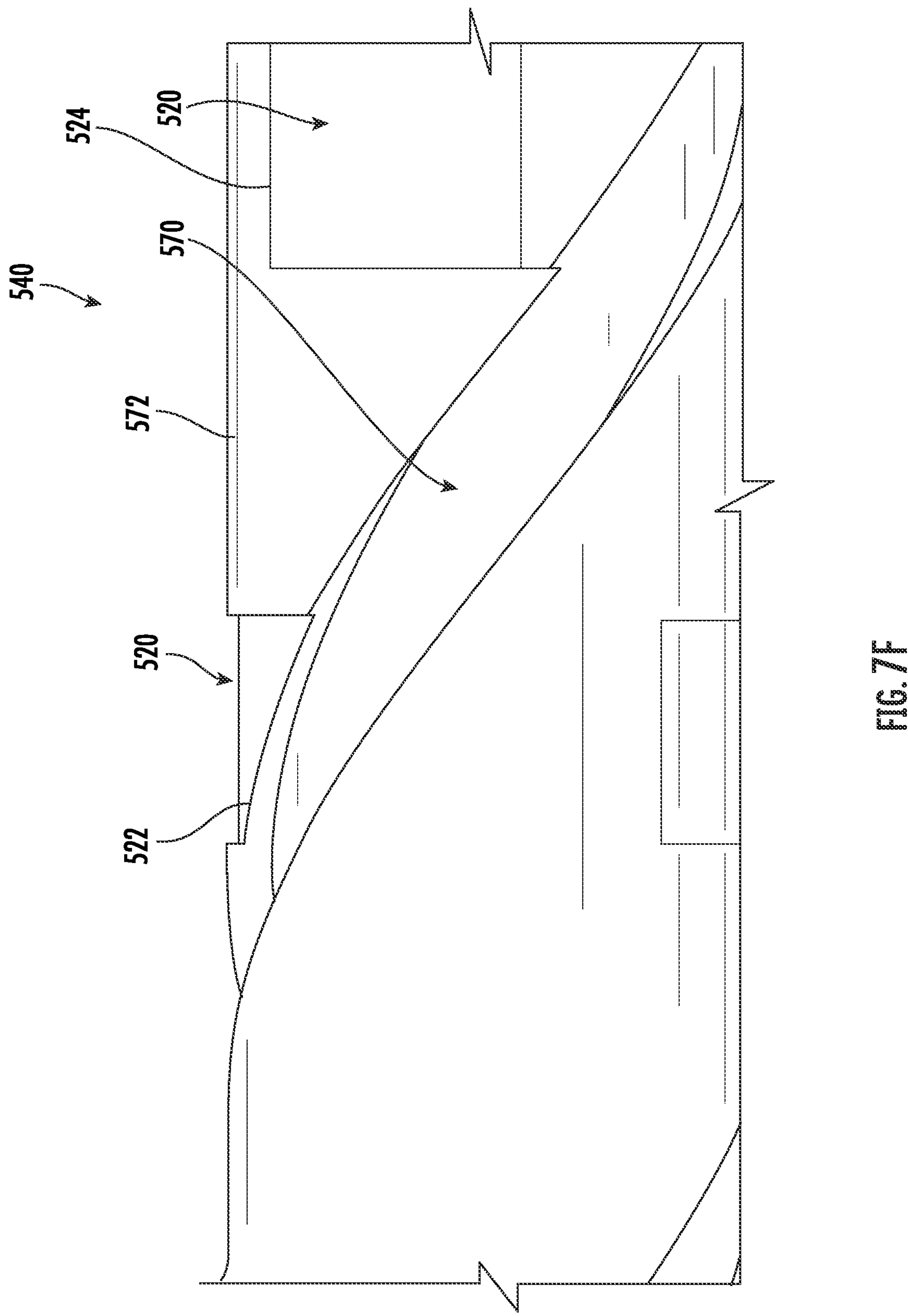
FIG. 7F is an enlarged view of one portion of the rotor of FIG. 7D.

Referring now to FIGS. 7D-7F, another embodiment of an axial flow pump 500 will now be described. As in the previous embodiment, pump 500 includes an outer housing or casing 502 and a rotor 540 coupled to an impeller 550 and a stator or diffuser 560. Rotor 540 and impeller 550 may be coupled together by any suitable means, such as a threaded screw type connection 509 that allows rotor 540 to rotate impeller 550. Impeller 550 and stator 560 are rotatably coupled to each other with a rotational linkage 511 such that stator 560 remains stationary within housing 502 as impeller 550 rotates.

In this embodiment, rotor 540 includes one or more grooves, channels or the like 570 extending around an outer surface 572 of rotor 540. Groove 570 preferably extend around outer surface 572 in a spiral or helical direction similar to ribs 270 and function in the same manner to draw blood into a secondary flow path 530 that passes through a clearance 580 between rotor 540 and an inner surface 582 of housing 202.

Pump 500 comprises an enlarged bulb 592 coupled to, or integral with, rotor 540 and having an outer diameter larger than the outer diameter of rotor 540. Bulb 592 includes a surface 594 adjacent the outer surface of rotor 540 that is transverse to the flow of blood in secondary flow path 530. As in previous embodiments, this compresses the fluid creating a higher fluid pressure within this area. This higher fluid pressure applies a force against inclined surface 594 of bulb 592. The force applied against bulb 592 is in the opposite direction of forces applied by impeller 550 and rotor 540 and therefore at least partially resists these axial forces to maintain the axial position of impeller 550 and rotor 540 relative to housing.

Referring now to FIGS. 7E and 7F, rotor 540 further comprises a plurality of variable pressure surfaces 520 that are spaced from each other both longitudinally and circumferentially with respect to rotor 540. Variable pressure surfaces 520 each have a first end 522 adjacent groove 570 and a second end 524 circumferentially spaced away from groove 570 such that the surfaces 520 extend from groove 570 to a portion of outer surface 572 between adjacent spirals of the groove 570.

As shown more clearly in FIG. 7F, variable pressure surfaces 520 are at least partially recessed from the outer surface 572 of rotor 550. Specifically, surfaces 520 are angled in the circumferential direction such that second end 524 is substantially parallel with the outer surface of 572 of rotor and first end 522 extends inwardly at an angle relative to outer surface 572. Thus, first end 522 is recessed from outer surface 572 and gradually angles upward relative to surface 572 until it joins with the outer surface and is no longer recessed. This creates a greater cross-sectional area between the inner surface 582 of housing 502 at first end 522 of pressure surface 520 than the cross-sectional area between inner surface 582 of housing and second end 524 of housing. Also, the cross-sectional area between first end 522 and inner surface 582 is greater than the cross-sectional area of clearance 580 (see FIG. 7D).

In the event that any portion of rotor 540 moves closer to inner surface 582 of housing 502 (i.e., such that the clearance 580 becomes smaller at that location), the variable pressure surfaces 520 compress the blood flowing past them at the circumferential location that is closest to inner surface 582 of housing 502 to generate a force opposing this motion. This radial force resists the radial force or motion that is moving the rotor towards the housing and would otherwise destabilize the radial position of rotor 540 within housing 520.

Rotor 540 may also include a hub 581 that functions similar to enlarged portion 592 of to provide a relatively high fluid pressure region that creates stabilizing axial forces. For example, hub 581 is designed with a smaller outer diameter than the remainder of rotor 540. In this configuration, hub 581 and rotor 540 define an inclined surface 593 therebetween. Inclined surface 593 may be configured to create a clearance between hub 581 and the inner surface of housing 502 that has a smaller cross-sectional area than the cross-sectional area of clearance 580. Similar to the above description of enlarged portion 592, this increases the fluid pressure within this clearance and applies a force against inclined surface 593.

In some embodiments, intracardiac device 200 may include one or more mechanical bearings to, for example, maintain the axial and radial positions of impeller 250 and rotor 240 when motor is operating at RPMs that are below a threshold to achieve the variable pressures described above. In this mode of operation, the lower rotational speed of the motor results in a reduced flow velocity of blood through the clearance between rotor 240 and casing 202. This reduced velocity may reduce the effectiveness of the variable pressure surfaces described above. For example, when the motor is first turned on, there is a delay in time before the motor is operating at the prescribed RPM. During this time, the radial or axial forces against the impeller and rotor may be greater than the offsetting forces provided by the variable pressure surfaces.

Figure 8D:
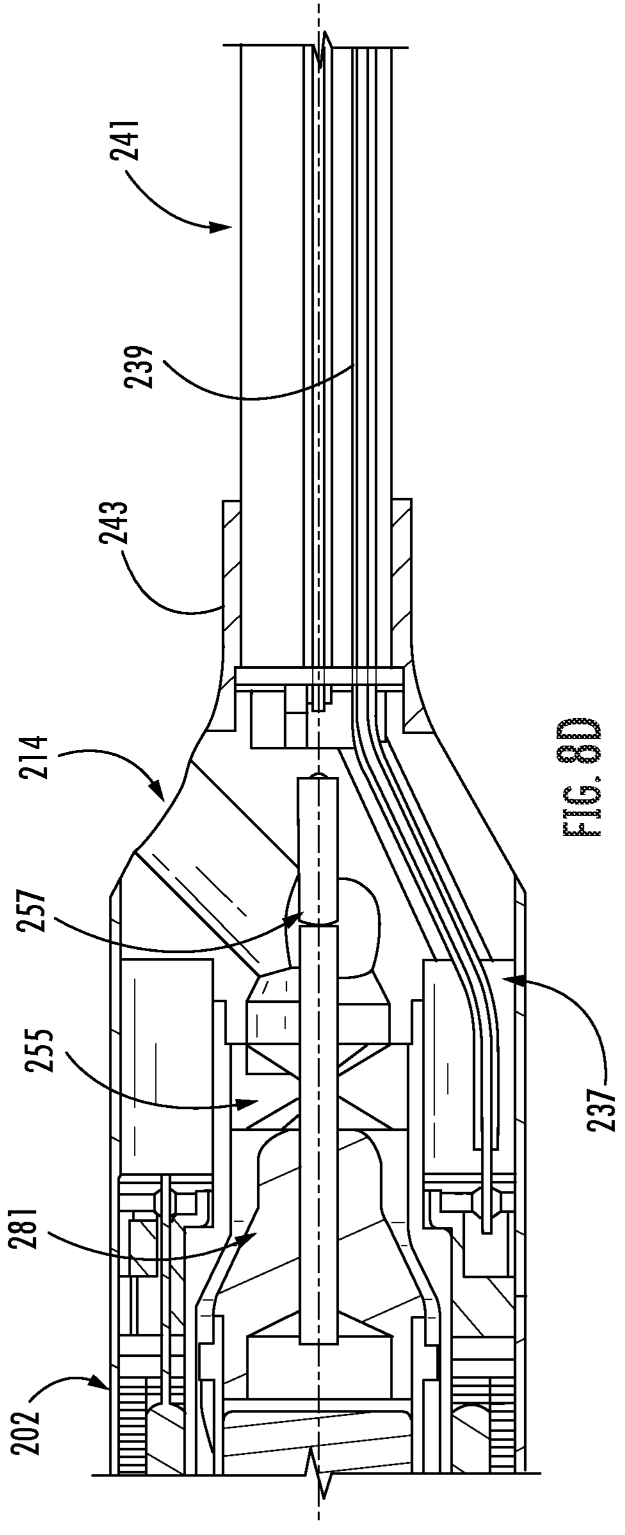
FIG. 8D is an enlarged cross-sectional view of a backend portion of the pump of FIG. 6.

In one such embodiment shown in FIG. 8D, device 200 includes a radial bearing 255 coupled to hub 281 positioned at the end of rotor 240 opposite impeller 250. Device 200 may further comprise a ball and cup bearing 257 for providing axial stability when the motor is operating below a threshold RPM.

Figure 9:
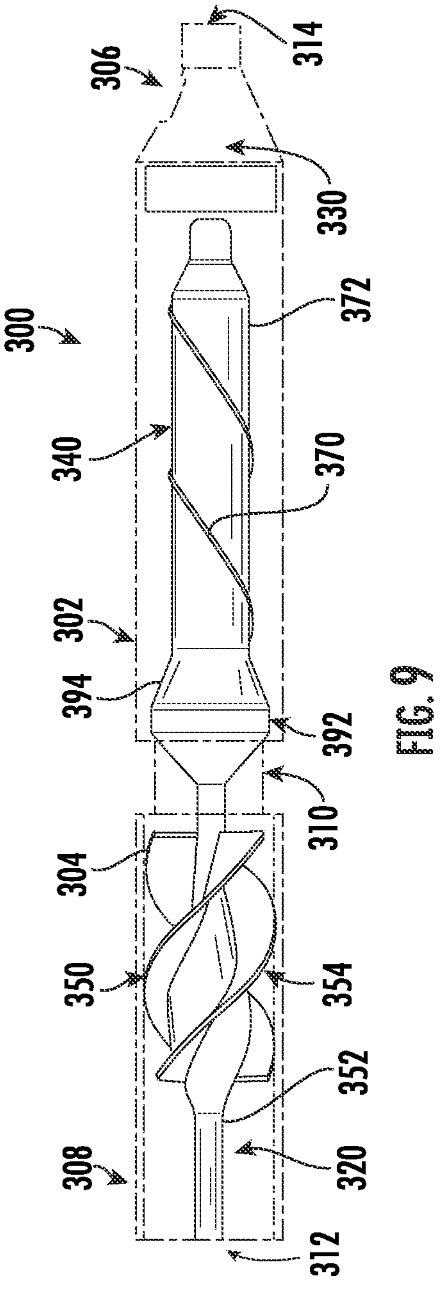
FIG. 9 is a side view of another embodiment of an axial flow pump.

Referring now to FIG. 9, an alternative embodiment of an intracardiac device 300 includes an outer casing 302 having a substantially cylindrical main body 304 with first and second ends 306, 308. Main body 304 may have a substantially uniform outer diameter to facilitate insertion of device 300 into a blood vessel or specific delivery device. Main body 304 includes an inlet 310 located between first and second ends 306, 308, a first outlet 312 at, or near, second end 308 and a second outlet 314 at, or near, first end 306. Inlet 310 and first outlet 312 are fluidly coupled to each other to define a primary blood flow path 320 through an internal lumen in casing 302. Inlet 310 is also fluidly coupled to second outlet 314 to define a secondary blood flow path 330 through an internal lumen of casing 302.

Device 300 further includes a motor stator (not shown) that is preferably integral with outer casing 302 and may include stator windings and a back iron. A tubular rotatable element 340 is positioned within casing 302 between inlet 310 and second outlet 314. Rotatable element or rotor 340 is configured to be rotated (i.e., driven) by the motor stator. In one embodiment, the motor stator includes one or more permanent magnets and rotatable element 340 includes one or more magnets such that rotatable element 340 may be rotated by a suitable magnetic field, as is known in the art.

Rotor 340 is coupled to an impeller 350 that comprises a hub 352 and one or more rotating blades 354 for drawing blood through inlet 310. Device 300 may further include a diffuser or stator (not shown) that is configured to redirect blood flow from the radial direction to the longitudinal direction and to reduce turbulence of the blood flow passing through blades 354 and into outlet 312. In one embodiment, blades 354 have a substantially helical shape such that the blades 234 spiral around hub 352 from the upstream end to the downstream end.

Rotor 340 preferably includes one or more ribs 370 (or channels) extending from an outer surface 372 thereof. Ribs 370 may comprise blades, vanes, fins or other projections that extend around outer surface 372 and are configured to draw fluid into casing from inlet 310 as element 340 rotates around its longitudinal axis. Ribs 370 preferably have a substantially helical shape with generally the opposite orientation as impeller blades 354 such that the flow of blood in secondary blood flow path 330 is in substantially the opposite direction as primary blood flow path 320. Similar to the device shown in FIGS. 6-8, rotor 240 defines a clearance (not shown) between its outer surface and the inner surface of casing 202.

The blood flowing through secondary flow path 330 creates a force against device 300 that is in the opposite direction as the force created by the blood flowing through impeller 354 in the primary blood path 320. The mass flow rate of the blood in secondary flow path 330 is significantly less than the mass flow rate of the blood in primary flow path 320 in order to ensure that the majority of the power applied to pump 300 is consumed with the primary goal of propelling blood through the primary flow path and into the aorta to support function of the left ventricle. In certain embodiments, mass flow rate of the blood in secondary flow path is about 1% to about 20%, preferably about 5% to about 10%, of the mass flow rate of the blood in primary flow path 320.

Since the mass flow rate of the secondary flow path is less than the primary flow path, additional forces must be applied to maintain axial stability of the rotor and impeller. To that end, device 300 includes one or more fluid pressure elements that provides resistance to the flow of blood along secondary flow path 330. This resistance at least partially offsets these axial forces and serves to arrest the forward translation of rotor 340 and impeller 350 within casing 302.

In one embodiment, the fluid pressure elements comprises an enlarged bulb 392 coupled to, or integral with, rotor 340 and having an outer diameter larger than the outer diameter of rotor 340. Bulb 392 includes an outer surface 396, a first inclined surface 394 adjacent the outer surface of rotor 340 that is transverse to the flow of blood in secondary flow path 330 and a second inclined surface 398 adjacent inlet 310. Outer casing 302 includes a substantially cylindrical inner surface 382 that surrounds rotor 340 to provide clearance 380. This inner surface 382 includes an inclined portion 399 that extends alongside inclined surface 394 of bulb 392 to form a clearance 395 therebetween.

Clearance 395 has a smaller cross-sectional area than clearance 380. Thus, fluid flowing clearance 395 is compressed creating a higher fluid pressure within this area. This higher fluid pressure applies a force against inclined surface 394 of bulb 392. The force applied against bulb 392 is in the opposite direction of forces applied by impeller 350 and rotor 340 and therefore at least partially resists these axial forces to maintain the axial position of impeller 350 and rotor 340 relative to housing.

Figure 10:
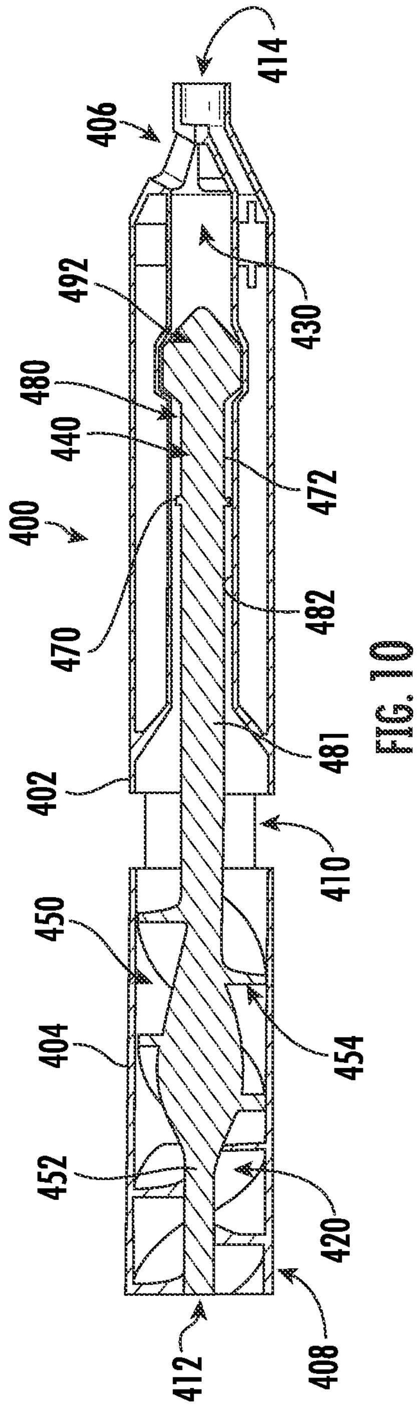
FIG. 10 is a cross-sectional view of another embodiment of an axial flow pump.

Referring now to FIG. 10, another embodiment of an intracardiac device 400 comprises an outer casing 402 having a substantially cylindrical main body 404 with first and second ends 406, 408. Main body 404 includes a first inlet 410 located between first and second ends 406, 408, an outlet 412 at, or near, second end 408 and a second inlet (or outlet) 414 at, or near, first end 406. First inlet 410 and outlet 412 are fluidly coupled to each other to define a primary blood flow path 420 through an internal lumen in casing 402. Second inlet (or outlet) 414 is fluidly coupled to either or both of first inlet 410 and outlet 412 to define a secondary blood flow path 430 through an internal lumen of casing 402

Similar to previous embodiments, device 400 also includes a motor stator (not shown) and a rotor 440 positioned within casing 402 between first and second inlets 410, 414. Rotor 440 is coupled to an impeller 450 that comprises a hub 452 and one or more rotating blades 454 for drawing blood through inlet 410. Rotor 440 preferably includes one or more ribs 470 extending from an outer surface 472 of rotatable element 440. Ribs 470 may comprise blades or other projections that extend around outer surface 472 and are configured to draw fluid into casing from inlet 410 as rotor 440 rotates around its longitudinal axis. Alternatively, ribs 470 may be oriented to draw blood from inlet 414. Ribs 470 preferably have a substantially helical shape and may be oriented in the same or the opposite direction as impeller blades 354, as described in the embodiments of FIGS. 7 and 9.

Rotor 440 defines a clearance 480 between its outer surface 472 and the inner surface 482 of casing 402. This clearance 480 provides the space for secondary blood flow path 430. Blood flowing through secondary flow path 430 ensures that rotatable element 440 does not contact casing 402.

In this embodiment, the fluid pressure element comprises an enlarged bulb 492 coupled to rotor 440 having an outer diameter larger than the outer diameter of rotatable element 440. Bulb 492 is located near second inlet 414 on the opposite side of rotor 440 from impeller 454. An axial magnetic bearing 481 is located on the side of rotatable element 440 adjacent to or near impeller 454. Locating axial magnetic bearing 481 closer to impeller reduces the distance of the magnetic field, thereby making it more efficient and requiring less power consumption to provide axial stability to the device.

Figure 11:
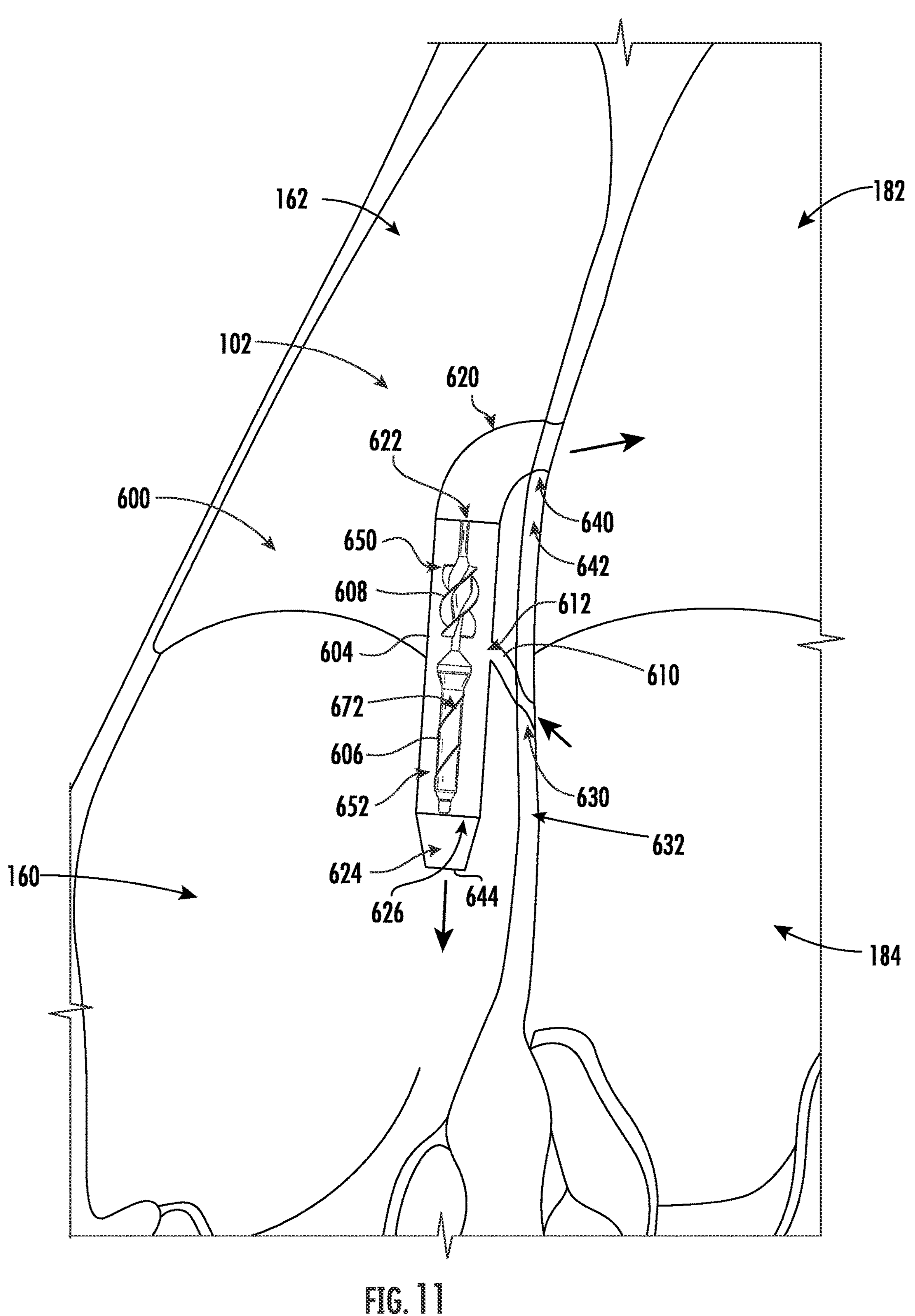
FIG. 11 is a schematic view of an axial flow pump in a right atrium of a patient's heart, illustrating a secondary flow path from the left atrium to the right atrium.

Referring now to FIG. 11, a system and method for supporting cardiac function with an implantable intracardiac device 600 will now be described. Device 600 is configured for implantation into the right atrium 160 and/or the SVC 162 of the patient. As discussed previously, device 600 includes an outer casing 604 enclosing a rotor 606 coupled to a motor stator (not shown) and an impeller 608. Device 600 further includes a first tube 610 attached to an inlet 612 within device 600 between rotor 606 and impeller 608, a second tube 620 attached to a first outlet 622 of device 600 and a third tube 624 attached to a second outlet 626 of device 600. Tubes 610, 620, 624 may be formed integrally with device 600, or they may be removably coupled to device 600 through any coupling device known to the art. One or all of the tubes may include a valve for opening and closing the fluid connection between the tube and device 600. The valve(s) may include sensors and may be controlled externally through the wireless power system described above.

In certain embodiments, device 600 includes one or more sensors (not shown) configured for detecting a physiological parameter of the right atrium, such as pressure, temperature or the like. The sensors are coupled to an internal or external controller (such as those described herein) and may be configured to transmit data related to the physiological parameter to the controller to allow for monitoring of these physiological parameters during operation of the device 600.

Device 600 further includes a first anchor 630 coupled to an inlet of first tube 610 and configured for anchoring tube 610 to a septal wall 632 between the right atrium and a left atrium 184 of the patient. Anchor 630 is configured to create a fluid passage through wall 632 such that blood may flow from left atrium 184 and into tube 610. A valve may be included within anchor 630 in addition to, or alternatively to, the valve coupling tube 610 to device 600. First anchor 630 may include one or more sensors (not shown) configured for detecting one or more physiological parameters of the left atrium and/or the right atrium. The sensors are coupled to the internal or external controller and may be configured to transmit data related to the physiological parameter to the controller to allow for monitoring of these physiological parameters during operation of the device 600. It may be particularly beneficial to monitor pressure within the left atrium as this pressure generally corresponds to pulmonary pressure. Pulmonary hypotension is a key physiologic parameter in monitoring heart failure patients. Traditional LVADs are not capable of monitoring left atrium pressure. The term “anchor” as used herein means any device or method for securing the tube to the wall, such as sutures, adhesives, self-expanding tubes, screw anchors, hook anchors, balloon anchors and the like.

Device 600 further includes a second anchor 640 coupled to an outlet of second tube 620 and configured for anchoring second tube 620 to a wall 642 between the SVC 162 and an aorta 182 of the patient. The valve may be included within anchor 640 in addition to, or alternatively to, the valve coupling tube 620 to device 600. Second anchor 640 may include one or more sensors (not shown) configured for detecting one or more physiological parameters of the SVC and/or the aorta. The sensors are coupled to the internal or external controller and may be configured to transmit data related to the physiological parameter to the controller to allow for monitoring of these physiological parameters during operation of the device 600.

Third tube 624 includes an outlet 644 that may be fluidly coupled with right atrium 602. Alternatively, outlet 626 of device 600 may simply have an open end coupled to right atrium 160 (i.e., without a tube extending therefrom).

Device 600 may further include one or more additional anchors (not shown) coupled to casing 602 and configured to secure device 600 to one or more of the inner walls of right atrium 160 and/or SVC 162.

Device 600 has a similar blood flow path as device 300 described above and shown in FIG. 10. Namely, impeller 608 creates a primary blood flow path 650 from left atrium 184, through first tube 610 and inlet 612 into device 600. The blood flows past impeller 608 through outlet 622 to second tube 620 and through anchor 640 into the aorta 182 of the patient. This primary blood flow path assists the heart by pumping blood from the left atrium directly into the aorta. The primary blood flow path bypasses the left ventricle and reduces the pre-load on the left ventricle, thereby supporting heart function.

In addition, device 600 creates a secondary blood flow path 652 from inlet 612 past rotor 606 and through second outlet 626 into tube 624, where it is propelled into right atrium 160. As discussed above, the secondary blood flow path 652 supports rotor 606 within casing (with no mechanical bearings), cleans blood and other debris form the clearance between rotor 606 and the casing 604 and at least partially offsets axial forces applied to device 600 by impeller 608.

The blood that exits tube 624 and into right atrium 160 will be oxygenated since it originated from the left atrium. Accordingly, it is important to minimize the mass flow rate of the blood passing through secondary flow path 652 to minimize the amount of oxygenated blood within the right atrium that will eventually travel through the patient’s lungs. Otherwise, the pump will require more power to pump enough blood into the aorta. To that end, secondary flow path 652 is configured to allow a mass flow rate of about 5% to about 10% of the mass flow rate of primary flow path 650.

Applicant has discovered that it may be advantageous to drive the blood from secondary flow path 652 into right atrium 602, rather than into aorta 642 or back into left atrium 634. This is because this blood is flushing out any blood or other debris within the clearance between rotor 606 and casing 602. If this blood or debris includes any blood clots, these clots will not pass into the aorta and the arteries supplying blood to the brain, which avoids the potential for a thrombotic stroke.

Figure 12:
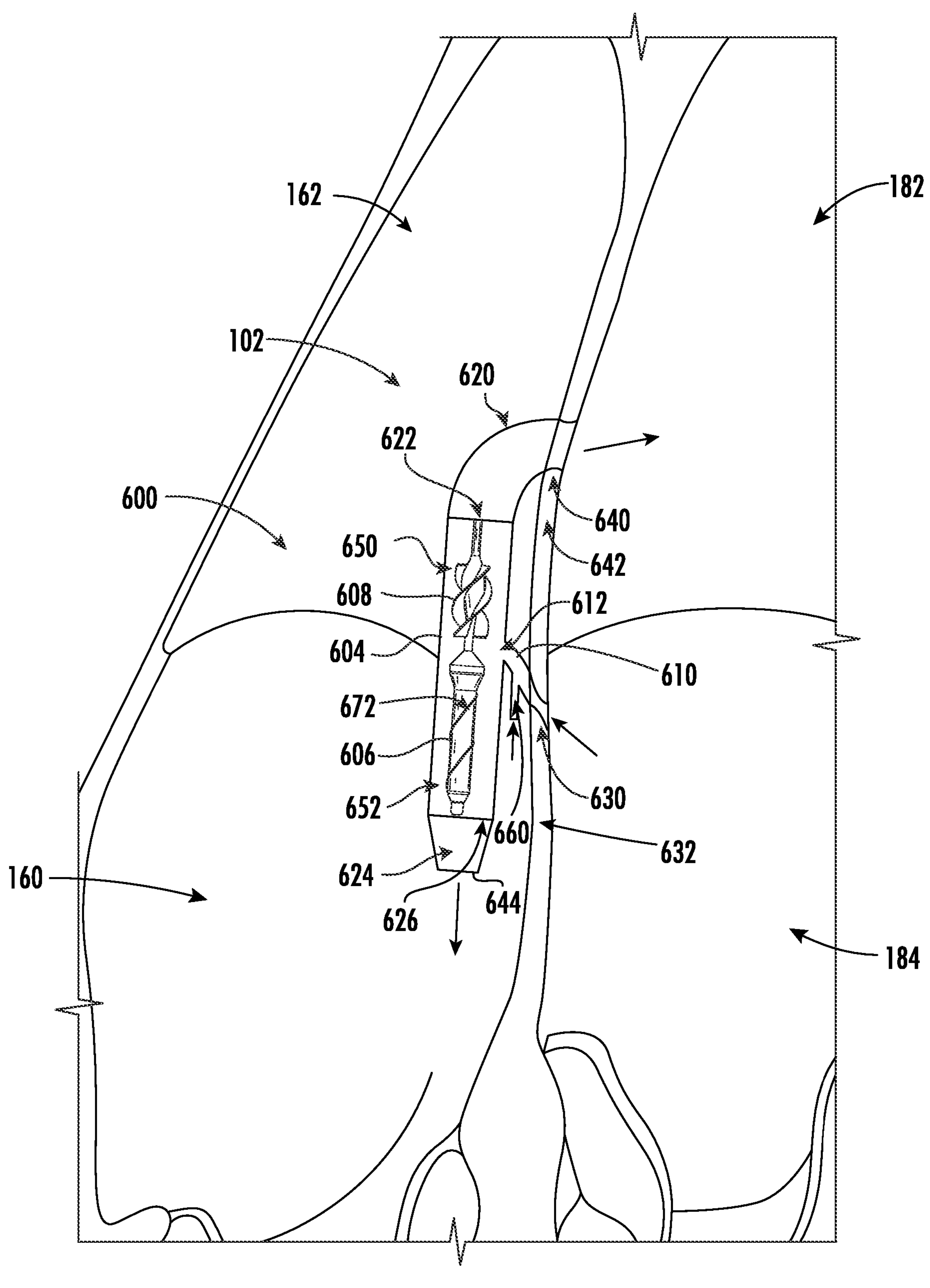
FIG. 12 is a schematic view of an axial flow pump in a right atrium of a patient's heart, illustrating a secondary flow path from the right atrium and back into the right atrium.

Referring now to FIG. 12, another embodiment of an implantable intracardiac device 600 for supporting cardiac function will now be described. Device 600 is configured for implantation into the right atrium 160 and/or the SVC 162 of the patient. As discussed previously, device 600 includes an outer casing 604 enclosing a rotor 606 coupled to a motor stator (not shown) and an impeller 608. Device 600 further includes a first tube 610 attached to an inlet 612 within device 600 between rotatable element 606 and impeller 608, a second tube 620 attached to a first outlet 622 of device 600 and a third tube 624 attached to a second outlet 626 of device 600.

Device 600 further includes a first anchor 630 coupled to an inlet of first tube 610 and configured for anchoring tube 610 to a septal wall 632 between the right atrium 602 and a left atrium 634 of the patient. Anchor 630 is further configured to create a fluid passage through wall 632 such that blood may flow from left atrium 634 and into tube 610.

Device 600 further includes a second anchor 640 coupled an outlet of second tube 620 and configured for anchoring second tube 620 to a wall between the SVC 162 and the aorta 182 of the patient. Third tube 624 includes an outlet 644 that may be fluidly coupled with right atrium 602.

In this embodiment, device 600 further includes a fourth tube 660 fluidly coupled to first tube 620 between anchor 630 and inlet 612 of device 600. The fourth tube 660 may be a separate tube that is connected to tube 610 through a suitable fluid connection, e.g., luer lock or the like. Alternatively, tubes 610 and 660 may be a single Y-shaped tube having two inlets and one outlet, as shown in FIG. 12.

In this embodiment, impeller 608 creates a primary blood flow path 650 from left atrium 634, through first tube 610 and inlet 612 into device 600. The blood flows past impeller 608 through outlet 622 to second tube 620 and through anchor 640 into the aorta of the patient. This primary blood flow path assists the heart by pumping blood from the left atrium directly into the aorta. The primary blood flow path bypasses the left ventricle and reduces the pre-load on the left ventricle, thereby supporting heart function.

In addition, device 600 creates a secondary blood flow path 652 from inlet 612 past rotor 606 and through second outlet 626 into tube 624, where it is propelled into the right atrium. As discussed above, the secondary blood flow path 652 supports rotor 606 within casing (with no mechanical bearings), cleans blood and other debris form the clearance between rotor 606 and the casing 604 and at least partially offsets axial forces applied to device 600 by impeller 608.

In this embodiment, inlet 612 may include separate passages coupling tube 610 with primary flow path 650 and tube 660 with secondary flow path 652. The separate passages may be included within 610 downstream of the Y-connection. Alternatively, tube 660 may enter device 660 in a separate inlet, e.g., between inlet 612 and rotor 606. This design ensures that the blood flowing from right atrium 602 passes only through secondary flow path 652. Likewise, the blood flowing from left atrium 634 only flows through primary flow path 650. This ensures that only oxygenated blood from the left atrium passes into the aorta and downstream through the arterial system. In addition, the blood from the right atrium is recirculated back into the right atrium, ensuring that the deoxygenated blood remains in the right side of the heart and any blood clots that are flushed from the pump remain on the right side of the heart.

Figure 13:
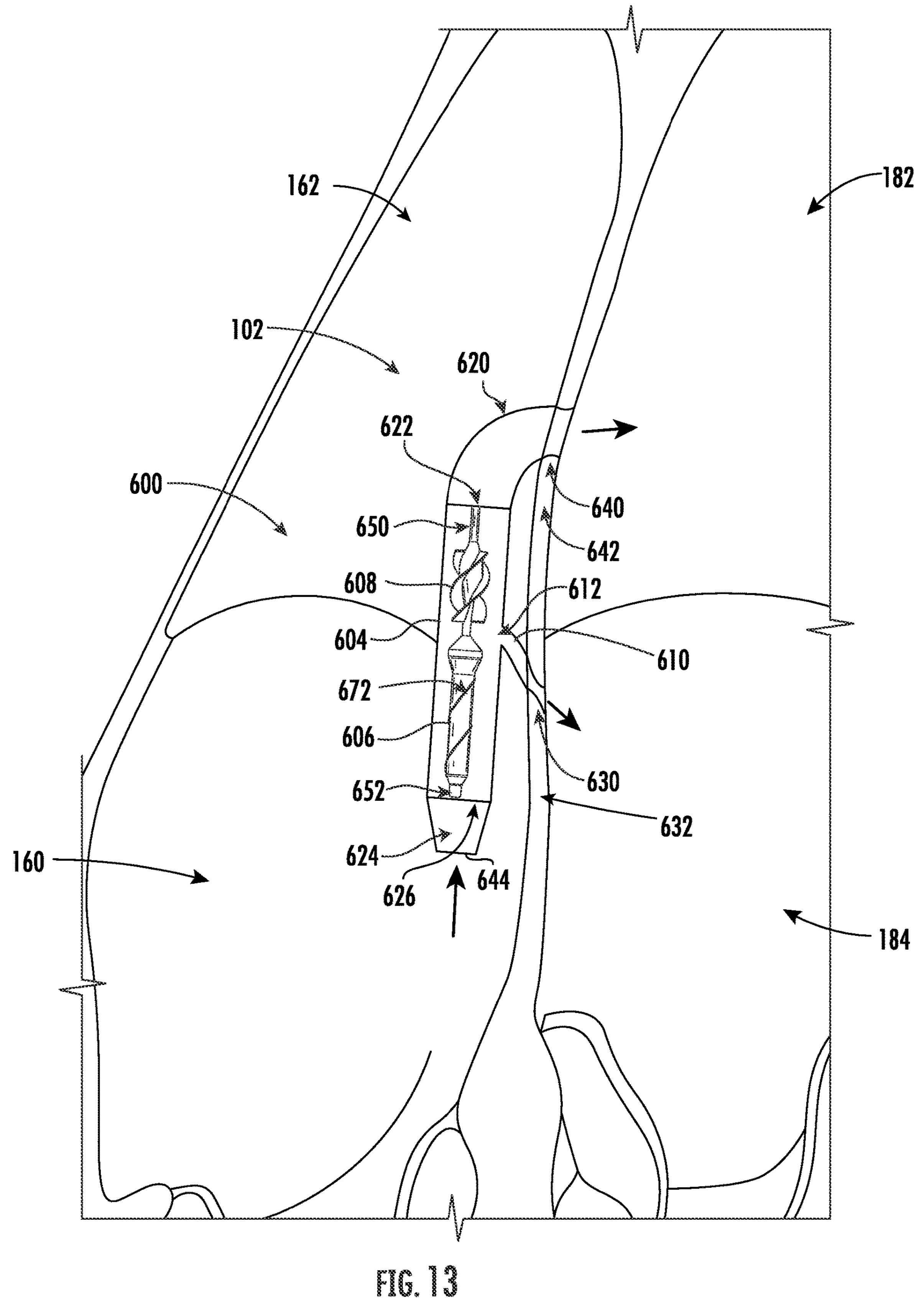
FIG. 13 is a schematic view of an axial flow pump in a right atrium of a patient's heart, illustrating a secondary flow path from the left atrium to the aorta.

Referring now to FIG. 13, device 600 has a similar construction as in FIG. 12 above except that the ribs 672 on rotor 606 form a reverse orientation so that the secondary blood flow path 652 is in substantially the same direction as the primary blood flow path 650. Thus, third tube 624 has an inlet 644 fluidly coupled to the right atrium 160 (rather than an outlet).

Impeller 608 creates primary blood flow path 650 from left atrium 184, through first tube 610 and inlet 612 into device 600. The blood flows past impeller 608 through outlet 622 to second tube 620 and through anchor 640 into the aorta 182 of the patient. In addition, device 600 creates a secondary blood flow path 652 from inlet 644 past rotatable element 606, where it joins the blood in primary blood flow path 650 and is propelled into the aorta.

This design causes both oxygenated and deoxygenated blood to flow into the aorta. As a result, the percentage of deoxygenated blood as compared to the oxygenated blood must be kept relatively low. Thus, rotor 606 is configured to draw a mass flow rate of blood through secondary blood flow path that is about 5% to about 10% of blood in the primary flow path.

In another embodiment, pump 600 may be configured such that a portion of the pump extends into left atrium 184. For example, inlet 644 of pump 600 may extend directly into left atrium 184 such that the blood flowing through secondary flow path 652 into the aorta 182 is oxygenated. In some embodiments, pump 600 is anchored across septal wall 632 such that an upstream portion of the pump 600 is disposed in left atrium 184 and a downstream portion of pump 600 is disposed in right atrium 160. In this embodiment, inlet 612 of the primary flow path 650 may also be disposed in left atrium 184, thereby obviating the need for tube 610 and anchor 630. This configuration also provides a stable anchoring point for pump 600 at septal wall 632.

Figure 14:
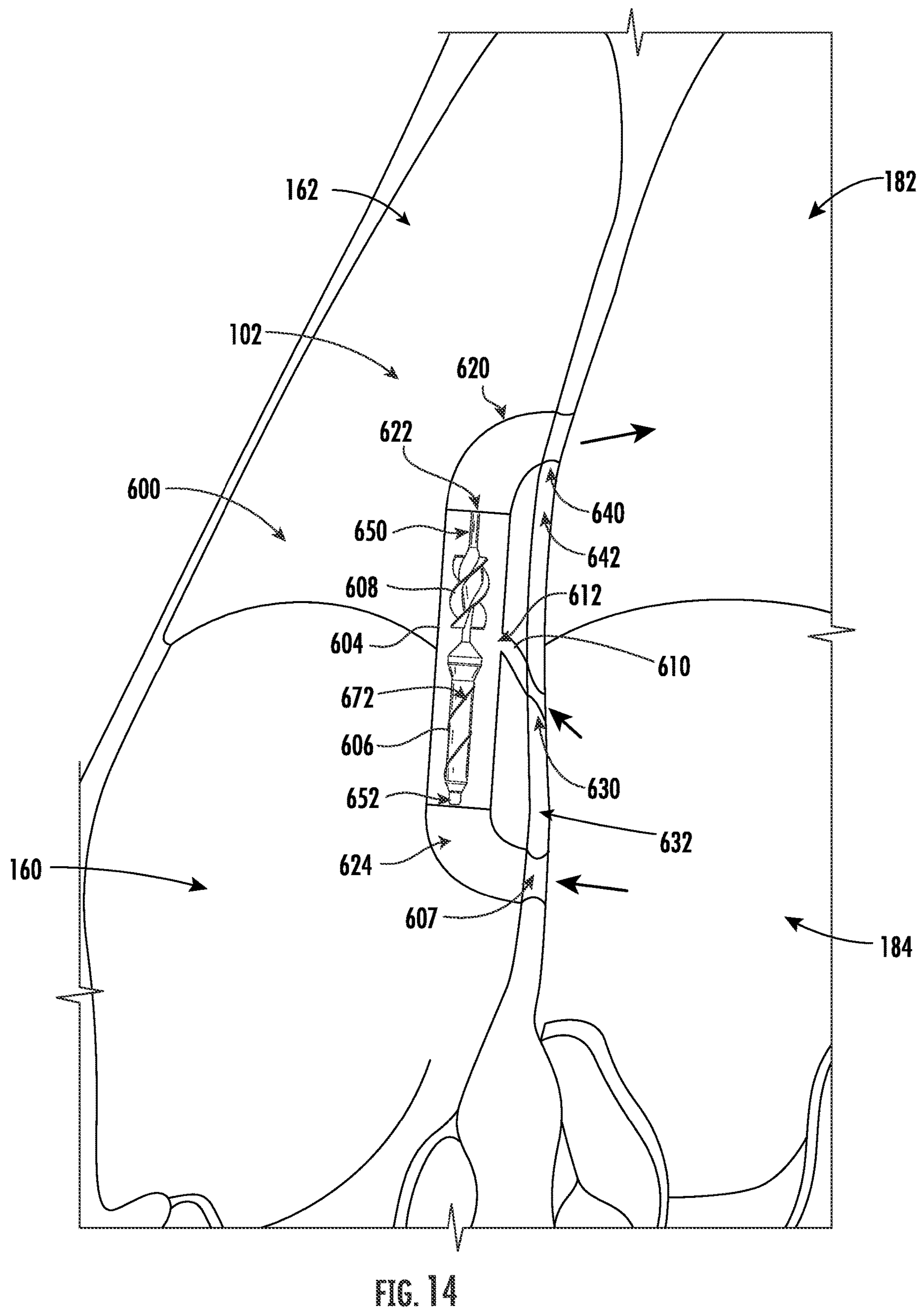
FIG. 14 is a schematic of an axial flow pump in a right atrium of a patient's heart, illustrating a secondary flow path from the left atrium to the aorta.

Referring now to FIG. 14, device 600 has a similar construction as in FIG. 12 above except that third tube 624 is coupled to a third anchor 670. Third anchor 670 is coupled to an inlet of third tube 624 and configured for anchoring tube 624 to septal wall 632 between the right atrium 602 and a left atrium 634 of the patient. Anchor 670 is further configured to create a fluid passage through wall 632 such that blood may flow from the left atrium and into tube 624. Thus, in this embodiment, blood flowing into both the primary and secondary blood flow paths is drawn from the left atrium and propelled directly into the aorta.

Similar to the embodiment shown in FIG. 13, the pump 600 in FIG. 14 may be anchored across septal wall 632 such that a portion of the pump is disposed within left atrium 184. This obviates the need for tubes 624, 610 and anchors 670, 630.

In other embodiments, the pumps described here may be entirely implanted in the left atrium 184. In these embodiments, pump 600 may include one or more tubes or anchors that direct the flow of blood from left atrium 184 through septal wall 632 and second tube 620 such that the blood flows through the wall between the SVC 162 and the aorta 182 of the patient. Alternatively, pump 600 may be configured to direct blood flow from the left atrium directly into the aorta (i.e., without passing into the right atrium or the SVC).

In yet another embodiment, the pumps described herein may be positioned in the left ventricle of the patient and configured to propel blood from the left ventricle directly into the aorta. In these embodiments, the pump may be configured for chronic longer-term implantation, as described above.

Alternatively, the pump may be configured for acute use for mechanical circulatory support of the heart, such as for the treatment of cardiogenic shock, to unload the ventricle and decrease myocardial oxygen consumption. In this embodiment, the pump may be placed percutaneously in the femoral artery using an introducer sheath and advanced in a retrograde fashion across the aortic valve into the left ventricle. In these embodiments, both the primary and secondary blood flow paths described above draw blood from the left ventricle. The secondary flow path may recirculate the blood back into the left ventricle, or it may direct the blood into the aorta along with the primary flow path.

Of course, it should be understood that the pumps described herein are not limited to implantation with the right atrium and/or the SVC.

Figure 15:
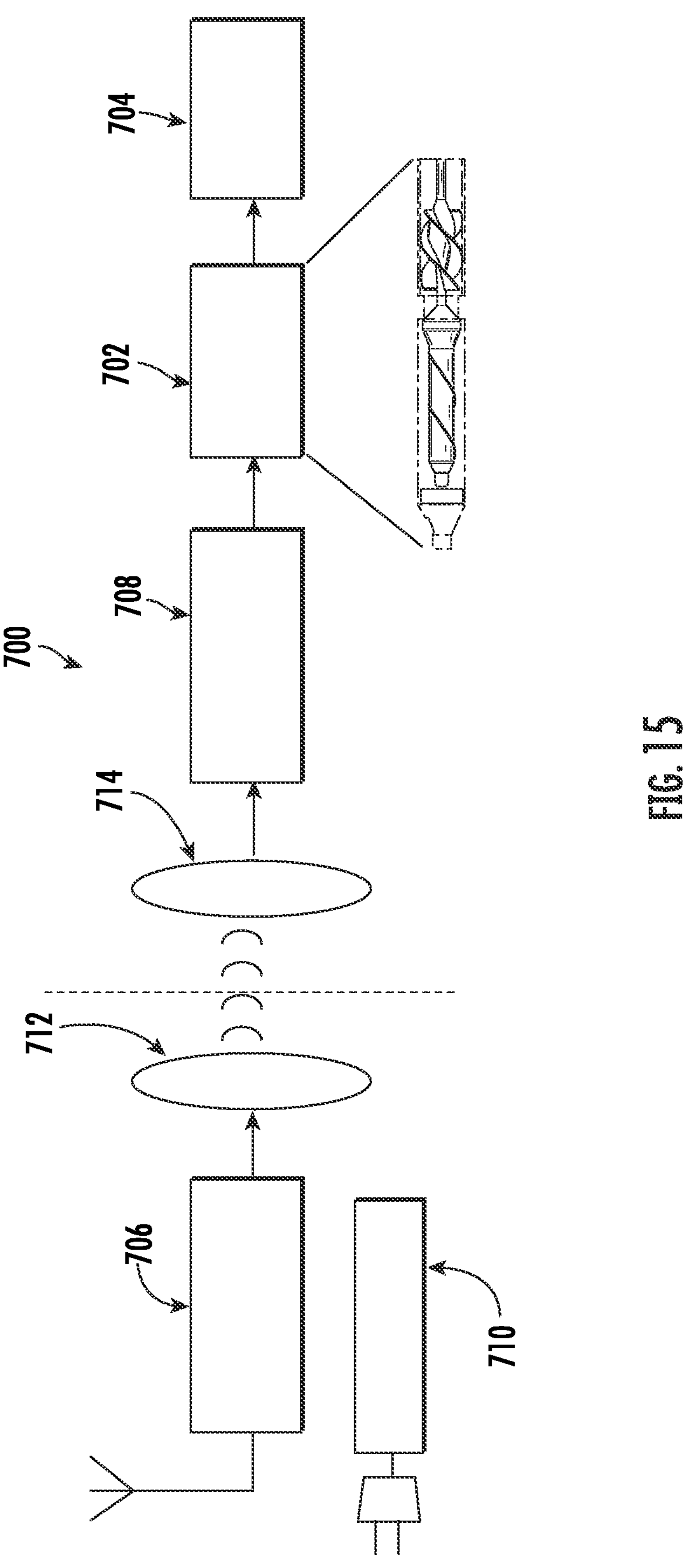
FIG. 15 is a flow chart illustrating various components of a ventricular assist system.

FIG. 15 is a flow diagram of ventricular assist system 700 that may include one or more of the axial flow pumps 702 described above. System 700 includes a wearable device 706 that comprises a wireless power transmitter, such as a magnetic coil, a power source, such as a rechargeable battery, an antenna and the associated electronics for transferring energy or power from the antenna to an internal controller 708. Wearable device 706 may also include a suitable coupler for removably coupling the power source to an external charger 710.

In certain embodiments, the wireless power transmitter within wearable device includes an amplifier or controller AC power supply that is operably coupled to a drive loop, to provide RF energy to the drive loop. A sensor, such as a directional coupler, vector network analyzer or the like, provides information from the drive loop.

Wearable device 706 may also include an attachment element (not shown) for attaching device to a patient. The attachment element may comprise any suitable releasable coupling element, such as fasteners, snaps, interference fit structures, Velcro and the like. Wearable device 706 may be configured for direct attachment to the patient's outer skin surface or for attachment to a variety of different wearable garments, such as pants, belts, hats, jackets, shirts, vests, shorts, skirts, bibs, coveralls. The wearable garment may include additional features, such as multiple hardpoints, straps or the like, for ensuring that the antenna contacts the patient's skin surface and engages this surface sufficiently to transmit the power therethrough with minimal losses. The wearable garment may also include a waterproof outer shell around to insulate the antenna, transmitter and associated electronic circuits from water or other fluids that may contact the garment.

The internal controller 708 that may be implanted in a suitable location within the patient. Controller 708 may be implanted subcutaneously within the patient, or it may be implanted within the patient's heart. Controller 708 comprises an antenna for receiving power from transmitter 706, a power source, such as a rechargeable battery, a motor driver for transferring the power to pump 702 and associated electronics, such as memory, telemetry and the like. Receiver 708 may further include one or more sensors that detect a variety of operational parameters for the pump 702, such as the power transmitted to the pump, the pump speed, the maximum output pressure, the negative intake pressure and the like.

In some embodiments internal controller 708 may include a load loop operably connected to provide energy to the pump 702, and a receiver resonator that is inductively coupled to the load loop. During operation, the transmitter resonator and the receiver resonator for a magnetically coupled resonator (MCR), such that the pump 702 is energized from RF energy from the amplifier that is inductively transmitted from the drive loop, to the MCR, and is inductively transmitted from the MCR to the load loop. A controller may be operable to receive data from the sensor, and to control the operating parameters to optimize the energy transfer efficiency in the MCR. A more complete description of a suitable wireless power transmitter can be found in U.S. Pat. No. 9,415,149, the complete disclosure of which is incorporated herein by reference in their entirety for all purposes.

Transmitter 706 is also configured to transmit various control signals to internal controller 708. Likewise, controller 708 is operable to control operation of pump 702 and to transmit data back to transmitter 706. The control signals provide feedback control to the pump based on physiological requirements of the patient. In some embodiments, the control signals are based on the power transferred to the receiver 708. These control signals may, for example monitor the dynamic power coupling between the transmitter and the receiver to ensure the efficient transfer of power therebetween.

Power may be transferred from wearable device 706 through the air 712 and the patient's tissue 714 to internal controller 708. In some embodiments, wearable device 706 may be in direct contact with the patient's tissue, which reduces or eliminates the amount of air 712 in the power transmission pathway. Internal controller 708 then transfers the power to the motor in pump 702, which drives the impeller and provides work to the blood 704 to propel the blood through pump 702. Power may be lost between all of these components due to various inefficiencies. For example, power may be lost between the receiver and transmitter due to a number of factors, including the distance between the coils, the offset between the center of the coils, the substance between the coils and the angle between the coils. The position and orientation of wearable device 706 may, therefore, change the efficiency of this power transfer, which may in turn effect the operation of pump 702. In certain embodiments, the wearable device 706 and/or the internal controller 708 include sensors (not shown) that detect the power transferred from wearable device 706 and the power received by internal controller 708. A controller (not shown) housed within, or coupled to, wearable device 706 calculates the difference between these two power values to ensure that the power loss remains within an acceptable range to operate pump 702.

In certain embodiments, the wearable device 706 and/or the internal controller 708 may also include sensors indicating the position and/or orientation of the wearable device 706 relative to the internal controller 708. The controller is configured to compare the position and orientation with the power loss to, for example, determine if the wearable device 706 is positioned correctly on the patient (i.e., at the optimal distance, angle and/or coil center offset to achieve an acceptable power transfer therebetween).

In one such embodiment, system 700 includes sensors that detect the physical distance between the antenna coils in wearable device 706 and internal controller 708. The sensors are coupled to the controller and configured to transmit this distance to the controller, either wirelessly, or through wearable device 706. The controller is configured to compare this distance with the power loss detected between the receiver and the transmitter to determine if the coils are, for example, positioned close enough to each other to provide sufficient power transfer to operate pump 702.

In another embodiment, system 700 includes one or more sensors that detect the relative angle of the coils in transmitter 706 and receiver 708. The sensors are coupled to the controller and configured to transmit this angle data to the controller. The controller is configured to compare this angle data with the power loss detected between the receiver and the transmitter to determine if the coils are, for example, oriented at an angle close enough to parallel to provide sufficient power transfer to operate pump 702.

In yet another embodiment, system 700 includes one or more sensors that detect the offset (if any) between the centers of the coils on the transmitter and the receiver. The sensors are coupled to the controller and configured to transmit this data to the controller. The controller is configured to compare this data with the power loss detected between the receiver and the transmitter to determine if the coils are, for example, centered relative to each other to provide sufficient power transfer to operate pump 702.

System 700 may further comprise a user interface (not shown) that includes one or more indicators coupled to the controller that indicate whether the wearable device is positioned at the optimal distance and/or orientation relative to the receiver 708. The indicators may be visual, audible, tactile (e.g., vibration) or the like, and they may be housed on, or within, wearable device 706 or wirelessly coupled to wearable device 706, for example, on a separate mobile device or the like. The user interface provides immediate feedback to the patient and/or the healthcare professional that the wearable device 706 should be repositioned to establish sufficient power transfer to pump 702.

In one such embodiment, the user interface includes one or more position indicators that indicate: (1) a distance between the wearable device 706 and the receiver 708; and/or (2) the positional offset between the centers of the coils in these two devices. The position indicator alerts the patient if the wearable device 706 is not positioned properly to achieve an efficient power coupling with the receiver 708.

In another embodiment, the wearable device 706 includes an angle indicator that alerts the patient of an unsuitable angle between the coils. Generally, the closer these two coils are to a parallel angle relative to each other, the less power will be lost during transfer. This angle indicator provides an alert to the patient if the wearable device 706 needs to be repositioned to reestablish this angle.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications, and variances. As well, one skilled in the art will appreciate further features and advantages of the present disclosure based on the above-described embodiments. Accordingly, the present disclosure is not to be limited by what has been particularly shown and described, except as indicated by the appended claims.

For example, in a first aspect, a first embodiment is a pump configured for implantation into a human heart or vascular system. The pump comprises an elongate housing having first and second ends, an internal surface, a first inlet for blood disposed between the first and second ends and an outlet spaced longitudinally from the first inlet. The first inlet and the outlet define a primary flow path through the housing. The pump includes a rotor disposed within the housing and spaced from the internal surface to define a clearance therebetween and an impeller coupled to the rotor for impelling blood from the first inlet to the outlet of the housing. The pump further includes a second inlet for blood within the housing fluidly coupled to the clearance between the rotor and the housing to define a secondary flow path through the clearance. The pump may be an axial flow pump.

A second embodiment is the first embodiment wherein the secondary flow path at least partially resists axial forces applied by impeller or the rotor.

A third embodiment is any one of the first two embodiments wherein the secondary flow path at least partially resists radial forces applied by the impeller or the rotor.

A fourth embodiment is any one of the first three embodiments wherein the secondary flow path provides a fluid bearing between the rotor and the housing.

A 5th embodiment is any one of the first 4 embodiments wherein the second inlet is disposed between the first and second ends of the housing.

A 6th embodiment is any one of the first 5 embodiments wherein the second inlet is disposed at, or near, the first end of the housing and the outlet is disposed at, or near, the second end of the housing.

A 7th embodiment is any one of the first 6 embodiments wherein the secondary flow path is in a substantially opposite direction as the primary flow path.

An 8th embodiment is any one of the first 7 embodiments wherein the secondary flow path is in a substantially same direction as the primary flow path.

A 9th embodiment is any one of the first 8 embodiments and further comprising a fluid pressure element in the secondary flow path.

A 10th embodiment is any one of the first 9 embodiments wherein the fluid pressure element comprises a surface extending in a lateral direction relative to a longitudinal axis of the housing.

An 11th embodiment is any one of the first 10 embodiments wherein the rotor comprises a substantially cylindrical outer surface and wherein the fluid pressure element comprises an enlarged portion of the rotor having a larger diameter than the rotor.

A 12th embodiment is any one of the first 11 embodiments wherein the enlarged portion comprises an angled surface extending from the cylindrical outer surface in a lateral direction relative to a longitudinal axis of the housing.

A 13th embodiment is any one of the first 12 embodiments wherein the enlarged portion defines a fluid channel between the angled surface and an inner surface of the housing, wherein the fluid channel has a cross-sectional area smaller than a cross-sectional area of at least one portion of the clearance.

A 14th embodiment is any one of the first 13 embodiments wherein the angled surface is located on the enlarged portion on an opposite side from the impeller.

A 15th embodiment is any one of the first 14 embodiments wherein the rotor comprises a substantially cylindrical outer surface and one or more variable pressure surfaces on the outer surface configured to resist radial forces.

A 16th embodiment is any one of the first 15 embodiments wherein at least a portion of the variable pressure surfaces are recessed from the outer surface of the rotor.

A 17th embodiment is any one of the first 16 embodiments wherein the variable pressure surfaces are circumferentially spaced from each other around the outer surface of the rotor.

An 18th embodiment is any one of the first 17 embodiments wherein the rotor comprises at least one rotational element for drawing blood into the secondary flow path.

A 19th embodiment is any one of the first 18 embodiments wherein the rotational element comprises a rib extending into the clearance between the rotor and the housing.

A 20th embodiment is any one of the first 19 embodiments wherein the rotational element comprises a groove in the outer surface of the rotor.

A 21st embodiment is any one of the first 20 embodiments wherein the rotor comprises an outer surface opposite the housing and at least one groove in the outer surface.

A 22nd embodiment is any one of the first 21 embodiments wherein the rotor and the impeller are suspended within the housing by the primary flow path and the secondary flow path.

A 23rd embodiment is any one of the first 22 embodiments and further comprising an electric motor stator within the housing for rotating the rotor.

In a second aspect, a first embodiment is a pump configured for implantation into a human heart or vascular system. The pump comprises an elongate housing having first and second ends, an internal surface, an inlet for blood disposed between the first and second ends and an outlet spaced longitudinally from the first inlet. The pump further comprises a rotor disposed within the housing and spaced from the internal surface to define a clearance therebetween, an impeller coupled to the rotor for impelling blood from the inlet to the outlet of the housing and a fluid bearing suspending the impeller and the rotor within the housing. The pump may be an axial flow pump.

A second embodiment is the first embodiment wherein the rotor and the impeller are spaced from the internal surface of the housing and at least partially supported with hydrodynamic forces within the housing.

A 3rd embodiment is any one of the first 2 embodiments wherein the fluid bearing comprises one or more surfaces that create a fluid pressure that resists axial forces generated by the impeller or the rotor.

A 4th embodiment is any one of the first 3 embodiments wherein the fluid bearing comprises one or more surfaces that create a fluid pressure that resists radial forces generated by the impeller or the rotor.

A 5th embodiment is any one of the first 4 embodiments wherein the housing defines a primary blood flow path between the inlet and the outlet, and further comprising a second inlet for blood within the housing fluidly coupled to the clearance between the rotor and the housing to define a secondary flow path through the clearance.

A 6th embodiment is any one of the first 5 embodiments wherein the secondary blood flow path is in a substantially opposite direction as the primary blood flow path.

A 7th embodiment is any one of the first 6 embodiments wherein the primary blood flow path has a first mass flow rate and the secondary blood flow path has a second mass flow rate, wherein the second mass flow rate is about 1% to about 20% of the first mass flow rate.

An 8th embodiment is any one of the first 7 embodiments wherein the second mass flow rate is about 5% to about 10% of the first mass flow rate.

A 9th embodiment is any one of the first 8 embodiments wherein the enlarged portion defines a fluid channel between the angled surface and an inner surface of the housing, wherein the fluid channel has a cross-sectional area smaller than a cross-sectional area of at least one portion of the clearance.

A 10th embodiment is any one of the first 9 embodiments wherein the angled surface is located on the enlarged portion on an opposite side from the impeller.

An 11th embodiment is any one of the first 10 embodiments wherein the rotor comprises a substantially cylindrical outer surface and one or more variable pressure surfaces on the outer surface configured to resist radial forces.

A 12th embodiment is any one of the first 11 embodiments wherein at least a portion of the variable pressure surfaces are recessed from the outer surface of the rotor.

A 13th embodiment is any one of the first 12 embodiments wherein the variable pressure surfaces are circumferentially spaced from each other around the outer surface of the rotor.

In a third aspect, a first embodiment is a method for supporting cardiac function in a patient. The method comprises positioning an axial flow pump within a heart chamber, the pump having a housing, a rotor within the housing and an impeller coupled to the rotor; rotating the impeller to draw blood through a primary flow path such that the blood flows through an outlet of the pump and into an aorta; and rotating the rotor to draw blood into a second inlet of the pump through a secondary flow path between the rotor and the housing.

A second embodiment is the first embodiment wherein the pump includes a rotor within a housing, the secondary flow path being disposed between the rotor and the housing.

A 3rd embodiment is any one of the first 2 embodiments wherein the secondary flow path is in a substantially opposite direction as the primary flow path.

A 4th embodiment is any one of the first 3 embodiments wherein the secondary flow path is in substantially the same direction as the primary flow path.

A 5th embodiment is any one of the first 4 embodiments and further comprising applying one or more forces against the blood in the secondary flow path to at least partially resist axial forces applied by the impeller or rotor.

A 6th embodiment is any one of the first 5 embodiments and further comprising applying one or more forces against the blood in the secondary flow path to at least partially resist radial forces applied by the impeller or rotor.

A 7th embodiment is any one of the first 6 embodiments and further comprising compressing the blood in one area of the secondary flow path to generate an axial force against a surface of the rotor.

An 8th embodiment is any one of the first 7 embodiments wherein the axial force maintains an axial position of the impeller and the rotor relative to the housing.

A 9th embodiment is any one of the first 8 embodiments and further comprising compressing the blood in a plurality of areas in the secondary flow path around the rotor to generate radial forces against the rotor.

A 10th embodiment is any one of the first 9 embodiments wherein the radial forces maintain a radial position of the impeller and the rotor relative to the housing.

In a fourth aspect, a first embodiment is a system for supporting cardiac function. The system comprises an elongate housing configured for implantation into a heart chamber of the patient. The housing has an inlet and an outlet spaced longitudinally from the inlet. The system further comprises a motor coupled to the housing, an impeller coupled to the motor and configured to propel blood through the primary blood flow path and a fluid bearing suspending the impeller and the rotor within the housing.

A second embodiment is the first embodiment and any of the preceding embodiments in the first aspect, the second aspect or the third aspect.

A $3^{rd}$ embodiment is any of the first and second embodiments, wherein the heart chamber is the right atrium and the inlet and the outlet define a primary blood flow path from a left atrium through at least a portion of the housing to an aorta.

A $4^{th}$ embodiment is any of the first 3 embodiments and further comprising a rotor disposed within the housing and spaced from an internal surface of the housing to define a clearance therebetween and a second inlet for blood within the housing fluidly coupled to the clearance between the rotor and the housing to define a secondary flow path through the clearance.

A $5^{th}$ embodiment is any of the first 4 embodiments wherein the secondary flow path at least partially resists axial forces applied by impeller or the rotor.

A $6^{th}$ embodiment is any of the first 5 embodiments wherein the secondary flow path at least partially resists radial forces applied by the impeller or the rotor.

A $7^{th}$ embodiment is any of the first 6 embodiments wherein the rotor and the impeller are spaced from the internal surface of the housing and at least partially supported with hydrodynamic forces within the housing.

An $8^{th}$ embodiment is any of the first 7 embodiments wherein the fluid bearing comprises one or more surfaces that create a fluid pressure that resists axial forces generated by the impeller or the rotor.

A $9^{th}$ embodiment is any of the first 8 embodiments wherein the fluid bearing comprises one or more surfaces that create a fluid pressure that resists radial forces generated by the impeller or the rotor.

What is claimed is:

1. A pump configured for implantation into a human heart or vascular system, the pump comprising:

an elongate housing having first and second ends, an internal surface, a first inlet for blood disposed between the first and second ends and an outlet spaced longitudinally from the first inlet, the first inlet and the outlet defining a primary flow path through the housing;

a rotor disposed within the housing and spaced from the internal surface to define a clearance therebetween;

an impeller coupled to the rotor for impelling blood from the first inlet to the outlet of the housing; and a second inlet for blood within the housing fluidly coupled to the clearance between the rotor and the housing to define a secondary flow path through the clearance, wherein the rotor comprises a substantially cylindrical outer surface and one or more variable pressure surfaces on the outer surface in contact with the secondary flow path and configured to resist radial forces.

2. The pump of claim 1, wherein the secondary flow path at least partially resists axial forces applied by impeller or the rotor.

3. The pump of claim 1, wherein the secondary flow path at least partially resists radial forces applied by the impeller or the rotor.

4. The pump of claim 1, wherein the secondary flow path provides a fluid bearing between the rotor and the housing.

5. The pump of claim 1, wherein the second inlet is disposed between the first and second ends of the housing.

6. The pump of claim 1, wherein the second inlet is disposed at, or near, the first end of the housing and the outlet is disposed at, or near, the second end of the housing.

7. The pump of claim 1, wherein the secondary flow path is in a substantially opposite direction as the primary flow path.

8. The pump of claim 1, wherein the secondary flow path is in a substantially same direction as the primary flow path.

9. The pump of claim 1, further comprising a fluid pressure element in the secondary flow path.

10. The pump of claim 9, wherein the fluid pressure element comprises a surface extending in a lateral direction relative to a longitudinal axis of the housing.

11. The pump of claim 9, wherein the rotor comprises a substantially cylindrical outer surface and wherein the fluid pressure element comprises an enlarged portion of the rotor having a larger diameter than the rotor.

12. The pump of claim 1, wherein at least a portion of the variable pressure surfaces are recessed from the outer surface of the rotor and wherein the variable pressure surfaces are circumferentially spaced from each other around the outer surface of the rotor.

13. The pump of claim 1, wherein the rotor comprises at least one rotational element for drawing blood into the secondary flow path.

14. The pump of claim 1, wherein the rotor comprises an outer surface opposite the housing and at least one groove in the outer surface.

15. The pump of claim 1, wherein the rotor and the impeller are suspended within the housing by the primary flow path and the secondary flow path.

16. A pump configured for implantation into a human heart or vascular system, the pump comprising:

an elongate housing having first and second ends, an internal surface, an inlet for blood disposed between the first and second ends and an outlet spaced longitudinally from the first inlet;

a rotor disposed within the housing and spaced from the internal surface to define a clearance therebetween;

an impeller coupled to the rotor for impelling blood from the inlet to the outlet of the housing;

a fluid bearing suspending the impeller and the rotor within the housing; and wherein the housing defines a primary blood flow path between the inlet and the outlet, and further comprising a second inlet for blood within the housing fluidly coupled to the clearance between the rotor and the housing to define a secondary flow path through the clearance, wherein fluid flows through the secondary blood flow path is in a substantially opposite direction as fluid flows in the primary blood flow path.

17. The pump of claim 16, wherein the rotor and the impeller are spaced from the internal surface of the housing and at least partially supported with hydrodynamic forces within the housing.

18. The pump of claim 16, wherein the fluid bearing comprises one or more surfaces that create a fluid pressure that resists axial forces generated by the impeller or the rotor.

19. The pump of claim 16, wherein the fluid bearing comprises one or more surfaces that create a fluid pressure that resists radial forces generated by the impeller or the rotor.

20. The pump of claim 16, wherein the primary blood flow path has a first mass flow rate and the secondary blood flow path has a second mass flow rate, wherein the second mass flow rate is 1% to 20% of the first mass flow rate.

21. The pump of claim 20, wherein the second mass flow rate is 5% to 10% of the first mass flow rate.

* * * * *